US008303946B2

(12) United States Patent
Brinton et al.

(10) Patent No.: US 8,303,946 B2
(45) Date of Patent: Nov. 6, 2012

(54) METHODS AND COMPOSITIONS FOR INHIBITION OF VIRAL REPLICATION

(75) Inventors: Margo A. Brinton, Decatur, GA (US); Wei Li, Wayland, MA (US)

(73) Assignee: Georgia State University Foundation, Inc., Atlanta, GA (US)

( * ) Notice: Subject to any disclaimer, the term of this patent is extended or adjusted under 35 U.S.C. 154(b) by 349 days.

(21) Appl. No.: 10/654,273

(22) Filed: Sep. 2, 2003

(65) Prior Publication Data

US 2004/0162252 A1  Aug. 19, 2004

Related U.S. Application Data

(60) Provisional application No. 60/407,105, filed on Aug. 30, 2002.

(51) Int. Cl.
*C12N 15/00* (2006.01)
*C12N 15/33* (2006.01)
*C12N 15/86* (2006.01)
*C12Q 1/68* (2006.01)
*C12Q 1/70* (2006.01)

(52) U.S. Cl. .................. 424/93.1; 424/93.21; 424/93.2; 435/456; 435/5; 435/6.1

(58) Field of Classification Search .................. 514/44; 435/194, 5; 424/218.1, 93.1, 93.2; 536/24.5
See application file for complete search history.

(56) References Cited

U.S. PATENT DOCUMENTS 5,798,245 A * 8/1998 Anderson et al. ............. 435/194

OTHER PUBLICATIONS

Jordan, I. et al. Ribavirin inhibits West Nile virus replication and cytopathic effect in neural cells (2000) The Journal of Infectious Diseases, vol. 182:1214-1217.*
Morrey, J.D. et al. Identification of active antiviral compounds against a New York isolate of West Nile virus (2002) Antiviral Reasearch 55: 107-116.*
Li, W. et al., The 3' stem loop of the West Nile virus genomic RNA can suppress translation of chimeric mRNAs (2001) Virology, 287: 49-61.*
Shi, P.Y., et al. Cell proteins specifically bind to West Nile virus minus-strand 3' stem-loop RNA (1996) Journal of Virology, 70(9):6278-6287.*
Blackwell, J.L. et al. BHK cell proteins that bind to the 3' stem-loop structure of the West Nile virus genome RNA (1997) Journal of Virology, 71(9):6433-6444.*
Brinton, M., Host factors involved in West Nile virus replication (Dec. 2001) Annals of the New york Academy of Sciences, 951:207-19.*
Li, W., et al., Cell proteins TIA-1 and TIAR interact with the 3' stem-loop of the West Nile virus complementary minus-strand RNA and facilitate virus replication (Dec. 2002) Journal of Virolgy, 76(23):11989-12000.*
Nguyen, H. et al. The growing family of interferon regulatory factors (1998) Cytokine and Growth Factor Reviews, 8(4):293-312.*
Yamshchikov, VF, et al., An infectious clone of the West Nile flavivirus (2001) Virology, 281:294-304.*
Men et al. J. Virol. 1996, vol. 70, No. 6, pp. 3930-3937.*
Verma et al Nature, 1997, vol. 389, 1997, pp. 239-242.*
Blackwell (b) J. Virol. 1995, vol. 69, No. 9, pp. 5650-5658.*
Geiss et al. Virology Journal 2005, vol. 2, No. 53, pp. 1-13.*
Davis et al. Annals Neurology 2006, vol. 60, No. 3, pp. 286-300.*
Jordan et al. J. Inf. Dis. 2000, vol. 182, pp. 1214-1217.*
Aigner A. Appl. Microbiol. Biotechnology 2007, vol. 76, pp. 9-21.*
Anderson, P., Kedersha, N. 2002. Stressful initiations. Journal of Cell Science 115:3227-3234.
Beck, A. R., Q. G. Medley, S. O'Brien, P. Anderson, and M. Streuli 1996. Structure, tissue distribution and genomic organization of the murine RRM-type RNA binding proteins TIA-1 and TIAR Nucleic Acids Res. 24:3829-35.
Beck, A. R., I. J. Miller, P. Anderson, and M. Streuli 1998 RNA-binding protein TIAR is essential for primordial germ cell development Proc Natl Acad Sci U S A. 95:2331-6.
Blackwell, J.L.. and M.A. Brinton, 1997 Translation Elongation Factor-1 Alpha Interacts with 3' stem-loop region of West Nile Virus Genomic RNA, J. Virol. vol. 71, No. 9 , 6933-6944.
Blyn, L. B., K. M. Swiderek, O. Richards, D. C. Stahl, B. L. Semler, and E. Ehrenfeld 1996. Poly(rC) binding protein 2 binds to stem-loop IV of the poliovirus RNA 5' noncoding region: identification by automated liquid chromatography-tandem mass spectrometry Proc Natl Acad Sci U S A. 93:11115-20.
Blyn, L. B., J. S. Towner, B. L. Semler, and E. Ehrenfeld 1997 Requirement of poly(rC) binding protein 2 for translation of poliovirus RNA J Virol. 71:6243-6.
Brand, S., and H. M. Bourbon 1993. The developmentally-regulated *Drosophila* gene rox8 encodes an RRM-type RNA binding protein structurally related to human TIA-1-type nucleolysins Nucleic Acids Res. 21:3699-704.
Brinton, M. A., 2002 The molecular biology of west nile virus: a new invader of the western hemisphere Annu. Rev. Microbiol. 56:371-402.
Brinton, M. A. 1997. Host susceptibility to viral disease, p. 303-328. In N. N. e. al (ed.), Viral pathogenesis. Lippincott-Raven Publishers, Philadelphia.
Brinton, M. A., and J. H. Dispoto 1988. Sequence and secondary structure analysis of the 5'-terminal region of flavivirus genome RNA Virology. 162:290-9.
Brinton, M. A., A. V. Fernandez, and J. H. Dispoto 1986. The 3'-nucleotides of flavivirus genomic RNA form a conserved secondary structure Virology. 153:113-21.
Burke, D. S., and T. P. Monath 2001. Flaviviruses, p. 1043-1125. In D. M. Knipe, and P. M. Howley (eds), Fields Virology. Lippencott Williams and Wilkins, Philadelphia.
Cok, J, S.J. Action, A.R. Morrison 2003 The proximal region of the 3'-untranslated region of cyclooxygenase-2 is recognized by a multimeric protein complex containing HuR, TIA-1, TIAR, and the heterogeneous nuclear ribonucleoprotein U.
Davanloo, P., A. H. Rosenberg, J. J. Dunn, and F. W. Studier 1984. Cloning and expression of the gene for bacteriophage T7 RNA polymerase Proc Natl Acad Sci U S A. 81:2035-9.
Davis, M. T., and T. D. Lee 1998. Rapid protein identification using a microscale electrospray LC/MS system on an ion trap mass spectrometer J Am Soc Mass Spectrom. 9:194-201.
Davis, M. T., and T. D. Lee 1997. Variable flow liquid chromatography-tandem mass spectrometry and the comprehensive analysis of complex protein digest mixtures J Am Soc Mass Spectrom. 8:1059-1069.

(Continued)

Primary Examiner — Maria Marvich
(74) Attorney, Agent, or Firm — Troy S. Kleckley, Esq.; Troutman Sanders LLP

(57) ABSTRACT

The present invention is directed to methods and compositions that are effective in the inhibition of viral replication. In particular, the methods and compositions are effective at interfering with the activity of host cell proteins required in viral replication. For example, an embodiment of the invention is directed to inhibition of flavivirus replication wherein the replication is effected by changing the normal interactions of the host cell protein TIAR or TIA-1.

8 Claims, 16 Drawing Sheets

OTHER PUBLICATIONS

Figure 1A:
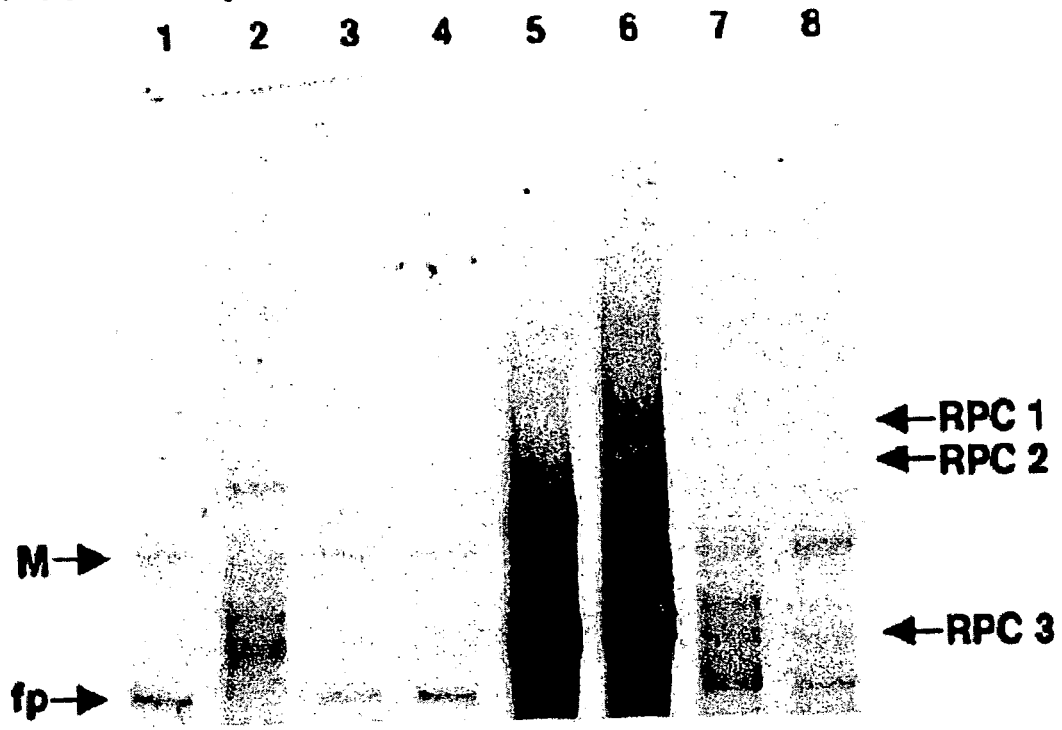

Del Gatto-Konczak, F., C. F. Bourgeois, C. Le Guiner, L. Kister, M. C. Gesnel, J. Stevenin, and R. Breathnach 2000. The RNA-binding protein TIA-1 is a novel mammalian splicing regulator acting through intron sequences adjacent to a 5' splice site Mol Cell Biol. 20:6287-99.

Dember, L. M., N. D. Kim, K. Q. Liu, and P. Anderson 1996. Individual RNA recognition motifs of TIA-1 and TIAR have different RNA binding specificities J Biol Chem. 271:2783-8.

Forch, P., and J. Valcarcel 2001. Molecular mechanisms of gene expression regulation by the apoptosis-promoting protein TIA-1 Apoptosis. 6:463-8.

Fukui, Y., S. Yumura, and T. K. Yumura 1987. Agar-overlay immunofluorescence: high-resolution studies of cytoskeletal components and their changes during chemotaxis Methods Cell Biol. 28:347-56.

Gueydan, C., L. Droogmans, P. Chalon, G. Huez, D. Caput, and V. Kruys 1999. Identification of TIAR as a protein binding to the translational regulatory AU-rich element of tumor necrosis factor alpha mRNA J Biol Chem. 274:2322-6.

Iseni, F., D. Garcin, M. Nishio, N. Kedersha, P. Anderson, and D. Kolakofsky, 2002. Sendai virus trailer RNA binds TIAR, a cellular protein involved in virus-induced apoptosis The EMBO Journal vol. 21, No. 19, pp. 5141-5150.

Jessen, T. H., C. Oubridge, C. H. Teo, C. Pritchard, and K. Nagai 1991. dentification of molecular contacts between the U1 A small nuclear ribonucleoprotein and U1 RNA Embo J. 10:3447-56.

Kawakami, A., Q. Tian, X. Duan, M. Streuli, S. F. Schlossman, and P. Anderson 1992. Identification and functional characterization of a TIA-1-related nucleolysin Proc Natl Acad Sci U S A. 89:8681-5.

Kedersha, N., C. Chen, N. Gilks, W. Li, I. J. Miller, J. Stahl and P. Anderson 2002. Evidence that ternary complex (eIF2-GTP-tRNA(i)(Met))-deficient preinitiation complexes are core constituents of mammalian stress granules Mol Biol Cell. 13:195-210.

Kedersha, N. L., M. Gupta, W. Li, I. Miller, and P. Anderson 1999. RNA-binding proteins TIA-1 and TIAR link the phosphorylation of eIF-2 alpha to the assembly of mammalian stress granules J Cell Biol. 147:1431-41.

Kim, Y. J., and B. S. Baker 1993. Isolation of RRM-type RNA-binding protein genes and the analysis of their relatedness by using a numerical approach Mol Cell Biol. 13:174-83.

Kotani, E., T. Ohba, T. Niwa, K. B. Storey, J. S. Storey, S. Hara, H. Saito, Y. Sugimura, and T. Furusawa 2003 De novo gene expression and antisense inhibition in cultured cells of BmTRN-1, cloned from the midgut of the silkworm, *Bombyx mori*, which is homologous with mammalian TIA-1/R. Gene Journal 320:67-9, Elsevier.

Lanciotti, R. S., J. T. Roehrig, V. Deubel, J. Smith, M. Parker, K. Steele, B. Crise, K. E. Volpe, M. B. Crabtree, J. J. Scherret, R. A. Hall, J. S. MacKenzie, C. B. Cropp, B. Panigrahy, E. Ostlund, B. Schmitt, M. Malkinson, C. Banet, J. Weissman, N. Komar, H. M. Savage, W. Stone,T. McNamara, and D. J. Gubler 1999. Origin of the west nile virus responsible for an outbreak of encephalitis in the northeastern united states Science. 286:2333-7.

Le Guiner C., M. C. Gesnel, and R. Breathnach 2003 TIA-1 or TIAR is required for DT40 cell viability. J Biol Chem. vol. 278, No. 12, pp. 10465-10476.

Le Guiner, C., F. Lejeune, D. Galiana, L. Kister, R. Breathnach, J. Stevenin, and F. Del Gatto-Konczak 2001. TIA-1 and TIAR activate splicing of alternative exons with weak 5' splice sites followed by a U-rich stretch on their own pre-mRNAs J Biol Chem. 276:40638-46.

Lewis, T., C. Gueydan, G. Huez, J. J. Toulme, and V. Kruys 1998. Mapping of a minimal AU-rich sequence required for lipopolysaccharide-induced binding of a 55-kDa protein on tumor necrosis factor-alpha mRNA J Biol Chem. 273:13781-6.

Li, W., Y. Li, N. Kedersha, P. Anderson, M. Emara, K. M. Swiderek, G. T. Moreno, and M. A. Brinton 2002 Cell proteins TIA-1 and TIAR Interact with the 3' stem-loop of the west nile virus complementary minus-strand RNA and facilitate virus replication J Virology vol. 76, No. 23 pp. 11989-12000.

Lindenbach, B. D., and C. M. Rice 2001. Flaviviridae: The viruses and their replication, p. 589-639. In D. M. Knipe, and P. M. Howley (eds), Fields Virology. Lippencott Williams and Wilkins, Philadelphia.

Lu, C. D., J. E. Houghton, and A. T. Abdelal 1992. Characterization of the arginine repressor from *Salmonella typhimurium* and its interactions with the carAB operator J Mol Biol. 225:11-24.

MacKenzie, J. M., M. K. Jones, and E. G. Westaway 1999. Markers for trans-Golgi membranes and the intermediate compartment localize to induced membranes with distinct replication functions in flavivirus-infected cells J Virol. 73:9555-67.

MacKenzie, J. M., A. A. Khromykh, M. K. Jones, and E. G. Westaway 1998. Subcellular localization and some biochemical properties of the flavivirus Kunjin nonstructural proteins NS2A and NS4A Virology. 245:203-15.

Men, R., M. Bray, D. Clark, R. M. Chanock, and C. J. Lai 1996. Dengue type 4 virus mutants containing deletions in the 3' noncoding region of the RNA genome: analysis of growth restriction in cell culture and altered viremia pattern and immunogenicity in rhesus monkeys J Virol. 70:3930-7.

Parquet, M. C., A. Kumatori, F. Hasebe, K. Morita, and A. Igarashi 2001. West Nile virus-induced bax-dependent apoptosis FEBS Lett. 500:17-24.

Piecyk, M., S. Wax, A. R. Beck, N. Kedersha, M. Gupta, B. Maritim, S. Chen, C. Gueydan, V. Kruys, M. Streuli, and P. Anderson 2000. TIA-1 is a translational silencer that selectively regulates the expression of TNF-alpha Embo J. 19:4154-63.

Rice, C. M. 1996. Fields Virology, 3rd Edition, pp. 931-959 Lippincott-Raven Publishers, Philadelphia.

Shi, P. Y., M. A. Brinton, J. M. Veal, Y. Y. Zhong, and W. D. Wilson 1996. Evidence for the existence of a pseudoknot structure at the 3' terminus of the flavivirus genomic RNA Biochemistry. 35:4222-30.

Shi, P. Y., W. Li, and M. A. Brinton 1996. Cell proteins bind specifically to West Nile virus minus-strand 3' stem-loop RNA J Virol. 70:6278-87.

Swiderek, K. M., M. T. Davis, and T. D. Lee 1998. The identification of peptide modifications derived from gel-separated proteins using electrospray triple quadrupole and ion trap analyses Electrophoresis. 19:989-97.

Taupin, J. L., Q. Tian, N. Kedersha, M. Robertson, and P. Anderson 1995. The RNA-binding protein TIAR is translocated from the nucleus to the cytoplasm during Fas-mediated apoptotic cell death Proc Natl Acad Sci U S A. 92:1629-33.

Tian, Q., M. Streuli, H. Saito, S. F. Schlossman, and P. Anderson 1991. A polyadenylate binding protein localized to the granules of cytolytic lymphocytes induces DNA fragmentation in target cells Cell. 67:629-39.

Tian, Q., J. Taupin, S. Elledge, M. Robertson, and P. Anderson 1995. Fas-activated serine/threonine kinase (FAST) phosphorylates TIA-1 during Fas-mediated apoptosis J Exp Med. 182:865-74.

Vaheri, A., W. D. Sedwick, S. A. Plotkin, and R. Maes 1965. Cytopathic effect of rubella virus in RHK21 cells and growth to high titers in suspension culture Virology. 27:239-41.

Weeks, K. M., and D. M. Crothers 1992. RNA binding assays for Tat-derived peptides: implications for specificity Biochemistry. 31:10281-7.

Wilson, R., R. Ainscough, K. Anderson, C. Baynes, M. Berks, J. Bonfield, J. Burton, M. Connell, T. Copsey, J. Cooper, et al. 1994. 2.2 Mb of contiguous nucleotide sequence from chromosome III of *C. elegans* Nature. 368:32-8.

Yu, Q., S. J. Cok, C. Zeng, A. R. Morrison, 2003 Translational repression of human matrix metalloproteinases-13 by an alternatively spliced form of T-cell restricted intracellular antigen-related protein (TIAR) J of Biological Chemistry, vol. 278, pp. 1579-1584.

Zeng, L., B. Falgout, and L. Markoff 1998. Identification of specific nucleotide sequences within the conserved 3'-SL in the dengue type 2 virus genome required for replication J Virol. 72:7510-22.

Zhang, T., V. Kruys, G. Huez, and C. Gueydan 2002. AU-rich element-mediated translational control: complexity and multiple activities of trans-activating factors. Biochemical Society Transactions, vol. 30, pp. 952-958.

Zhu, H., R. A. Hasman, K. M. Young, N. L. Kedersha, and H. Lou 2003. U1 snRNP-dependent function of TIAR in the regulation of alternative RNA processing of the human calcitonin/CGRP pre-mRNA.

* cited by examiner

A. Gel-Mobility shift assay

B. Coomassie blue staining

B.

US 8,303,946 B2

METHODS AND COMPOSITIONS FOR INHIBITION OF VIRAL REPLICATION

RELATED APPLICATIONS

The present invention claims priority to U.S. Provisional Patent Application No. 60/407,105, filed Aug. 30, 2002, which is herein incorporated in its entirety.

GOVERNMENT LICENSE RIGHTS

This invention was made with U.S. Government support under Grant Nos. AI018382 and GM054896 awarded by the National Institutes of Health. The U.S. Government has certain rights in the invention.

TECHNICAL FIELD

This invention is directed to methods and compositions for the inhibition of viral replication. In particular, the invention is directed to methods and compositions that interact with host proteins necessary for viral replication, or that interact with the viral nucleic acid to inhibit viral replication.

BACKGROUND OF THE INVENTION

Viruses cause some of the most debilitating illnesses known in humans, animals and plants. Vaccination procedures have provided some relief for humans and animals from some of the more deadly viruses, such as smallpox, measles, influenza and poliovirus. However, many viruses still cause much human suffering, loss of work days, death to animals and destruction of plants. Unlike bacteria, viruses use the host's own cellular mechanisms to reproduce.

Increased globalization has resulted in the invasion of new territories by viruses that were previously found only in specific geographic locations. A well known example of this is the spread of human immunodeficiency virus around the world. A recent example is the spread of West Nile virus into and through the United States.

West Nile virus is a mosquito-borne virus that was first isolated in 1937 from the blood of a patient in the West Nile region of Uganda. It has been endemic in parts of Africa, the Middle East and India. Wild birds are the main reservoir hosts, with human and horses acting as incidental hosts with no role in virus transmission.

West Nile virus (WNV) was first detected in the Western hemisphere in 1999, in New York state, United States. The mode of introduction of WNV into the United States is not known, but phylogenic analysis of the envelope gene of a WNV isolate indicates it was closely related to a WNV isolate in Israel. WNV transmission reoccurred in New York during the summers of 2000 and 2001, and the virus has spread southward and westward in the United States. It is expected that the virus will continue to spread throughout the United States, Canada, the Caribbean, and Central and South America. Mosquitoes capable of transmitting WNV to susceptible birds exist in all of these regions.

The incidence of clinical disease among WNV-infected humans is low, though in recent outbreaks there has been an increase in the severity of disease among those that develop clinical symptoms. Fever is the most common symptom, and other symptoms include headache, muscle weakness and disorientation. A few infected individuals develop encephalitis, meningoencephalitis, polio-like paralysis, Parkinson's disease-like symptoms or hepatitis. Most infected persons show no sign of infection. It is thought that in the 1999 outbreak in the U.S., 1900 persons were infected. Sixty-two developed clinical disease and of these, 7 died.

It is expected that microbial agents, such as viruses, will continue to be spread to new territories and that such agents will need to be identified and treatments provided to the unprotected populations. One method of protection, that would not be dependent on specific viral identification, would be to provide compositions that interact with host proteins that are commonly involved in the viral replication pathways of different related viruses, such as flaviviruses, to stop or interfere with viral replication.

What is needed are methods for identification of components of the viral replication cycle that can be interfered with or inhibited so that viral replication or the spread of infection in the host is interrupted, without harming the host, and the development of compositions that are effective in inhibiting or interfering with viral replication.

SUMMARY OF THE INVENTION

The present invention is directed to methods and compositions for inhibiting viral replication. Methods are described herein that identify proteins or regions of the viral nucleic acid that are important in viral replication. In particular, flavivirus replication is described wherein host proteins are important in replication of the virus. Methods of the present invention also include inhibiting the interactions of host proteins with viral components or inhibiting or interfering with viral nucleic acids to inhibit viral replication. Compositions comprising compounds, including nucleic acid constructs or small molecules that inhibit such viral replication are also included in the present invention.

Such compositions are easily administered by oral, subcutaneous, intravenous and routes known to those skilled in the art and can be given in dosages that are safe and provide inhibition of viral replication. The present invention provides methods of treating diseases, found in humans, animals and plants mediated by viral infection, comprising administering compositions comprising anti-viral compounds in dosages effective to inhibit viral replication.

FIGURES

FIG. 1, A-B show polyacrylamide gels showing gel mobility shift experiment results.

Figure 2:
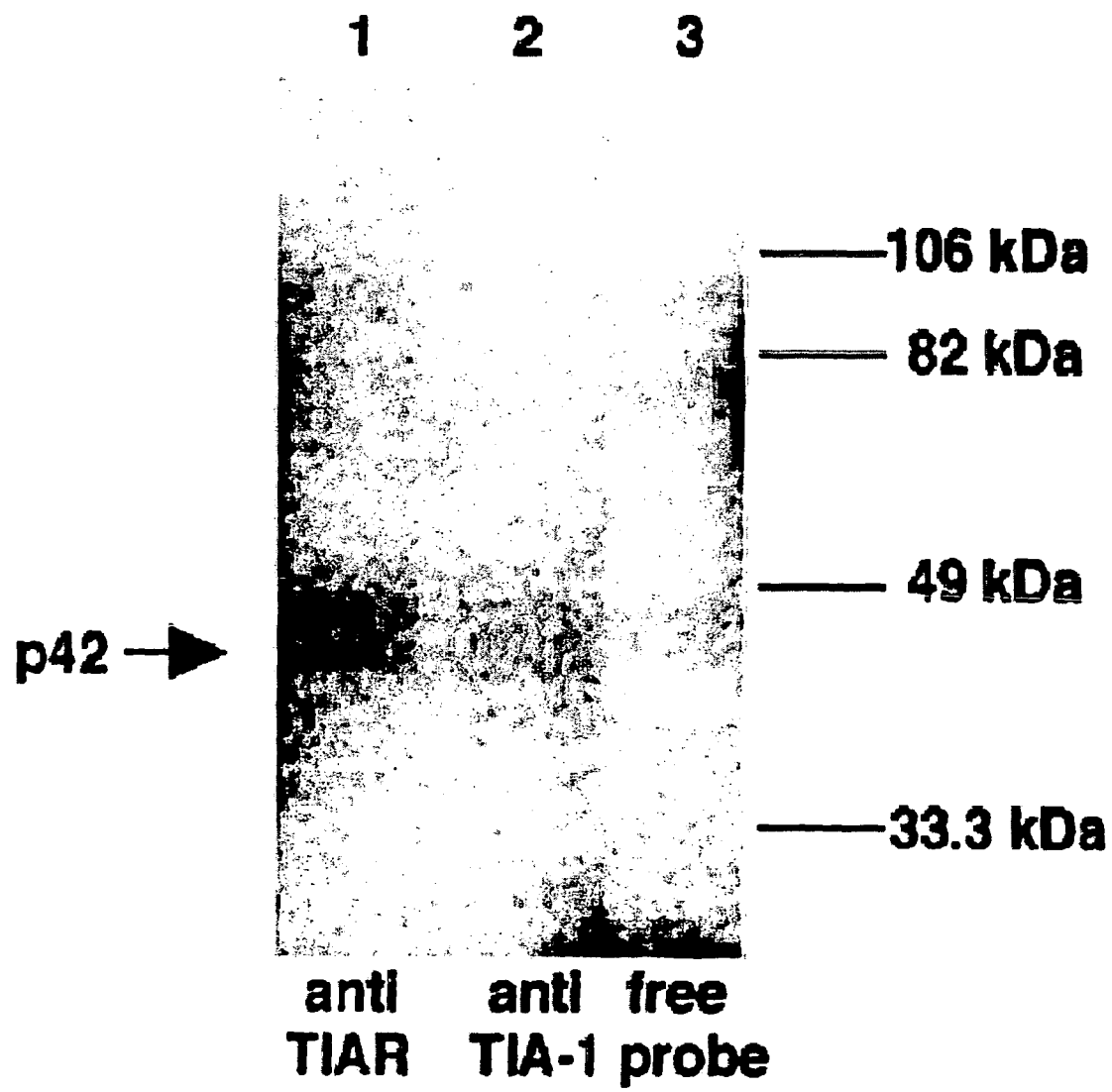

FIG. 2 shows immunoprecipitation of UV-induced cross-linking RNA-protein complexes by protein specific antibodies.

FIG. 3-A-D shows analyses of the specificity of the interactions between the WNV 3'(−) SL RNA and recombinant TIAR or TIA-1 proteins.

FIG. 4A-D shows quantification of the RNA-protein interactions.

FIG. 5A-F are graphs showing the growth of virus in TIAR or TIA-1-knockout cell lines.

FIG. 6A-F show Western blot analyses of the amounts of TIAR and TIA-1 proteins in various cell lines.

Figure 7:
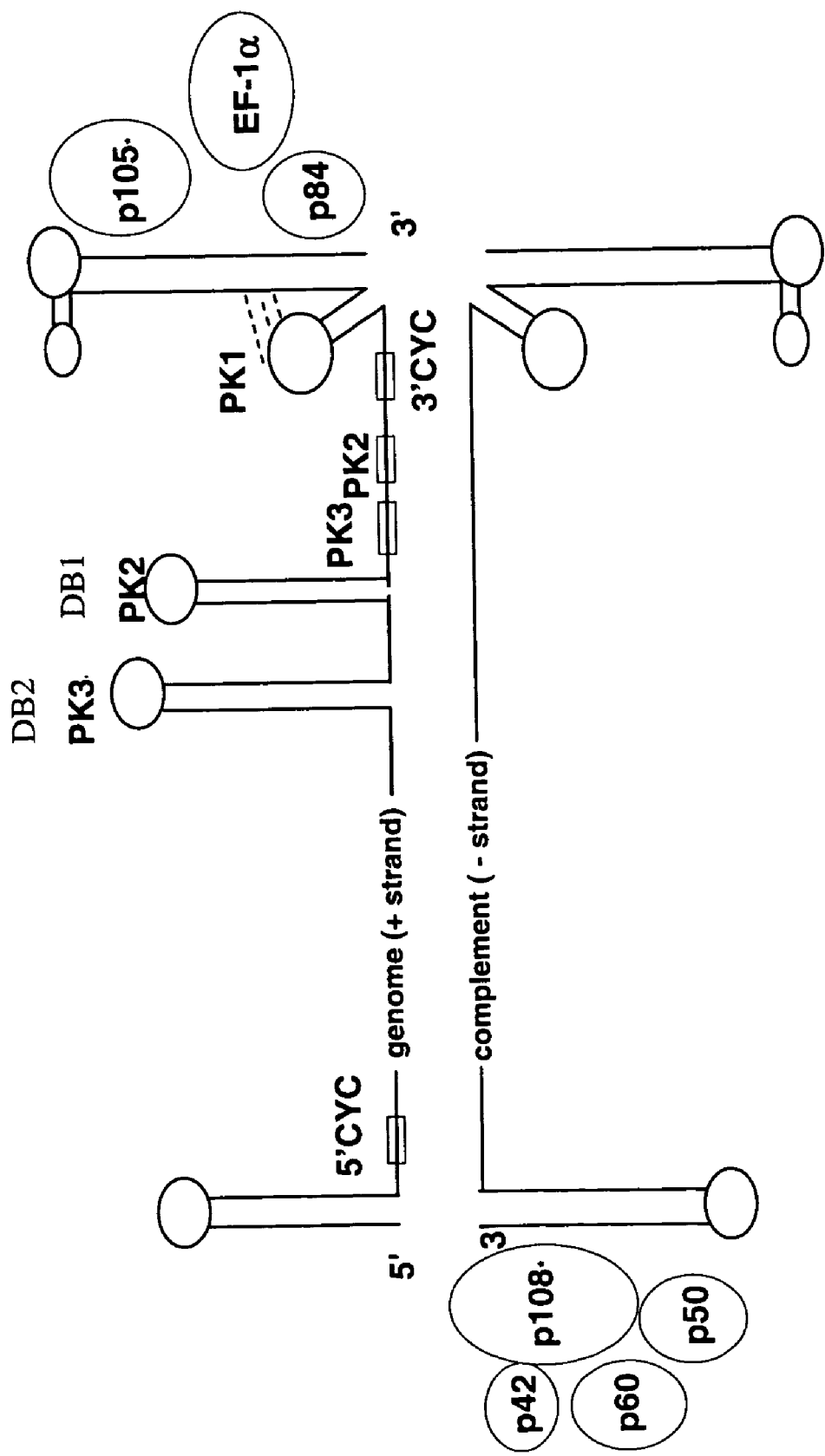

FIG. 7 is a schematic of host proteins interacting with WNV RNA.

DETAILED DESCRIPTION

The present invention is directed to methods and compositions that are effective in inhibiting viral replication. In particular, the present invention is directed to methods for identifying components of the viral replication cycle that are necessary for replication, such as proteins, and testing for compounds that are effective in the inhibition of these components. Inhibition of viral replication leads to little or no infected state in the organism, or reduces or terminates the infection in the organism.

Compositions and methods for the treatment of viral diseases that are mediated by inhibition of viral replication are also provided. Particularly, methods and compositions of the present invention are directed to inhibition of the activity of host cell proteins that are required for replication of viruses. Methods and compositions of the present invention are also directed to inhibiting or interfering with the viral nucleic acids to inhibit viral replication. Methods for the identification of cellular factors that are required to complete various steps of a virus lifecycle are also provided.

For example, one family of viruses that creates debilitating and deadly disease in humans and animals is Flaviviridae. This family consists of three genera, one of which is the genus Flavivirus. Flaviviruses are transmitted between bird and mammalian hosts via mosquitoes or ticks. Flaviviruses, such as dengue, Japanese encephalitis virus, West Nile virus (WNV), yellow fever virus, St. Louis encephalitis virus, Murray Valley encephalitis virus, and tick-borne encephalitis virus, can sometimes cause severe disease in infected humans (10, 24).

The genomes of flaviviruses are single-stranded, positive-polarity RNAs of approximately 11 kb and encode a single large polyprotein that is post-translationally processed by viral and cellular proteases into three structural proteins and seven non-structural proteins (34). During the flavivirus replication cycle, which takes place in the cytoplasm of infected cells, the genomic RNA (plus strand RNA) serves as the only viral mRNA and is also the template for transcription of the complementary minus-strand RNA. The minus-strand RNA in turn serves as a template for the synthesis of genomic RNA. Plus-strand RNA synthesis is 10 to 100 times more efficient than minus-strand synthesis (34).

The non-coding regions (NCRs) of the flavivirus genome contain terminal RNA structures that are conserved between divergent flaviviruses even though only short sequences in these regions are conserved (8, 9, 27, 36). The terminal RNA structures located at the 3' ends of the genome and complementary minus strand RNAs differ from each other in shape and size. Deletion or mutation of either 3' terminal structure in flavivirus infectious clones resulted in no progeny virus production and indicated that these regions were essential for virus replication (31, 45). However, specific cis-acting signal sequences within these structures have not yet been mapped nor functionally analyzed. The WNV 3' terminal RNA plus strand and minus strand RNA structures have previously been reported to bind specifically to different sets of cell proteins (3, 37; FIG. 7).

The present invention comprises methods and compositions that are effective in modifying the activity or interactions of components or proteins involved in the initiation and regulation of nascent genome RNA synthesis from the minus strand template, nascent minus strand RNA from the genome template, as well as translation of the viral RNA into protein and production of mature proteins for the virus. As used herein, inhibition or interference in viral replication means any change in the rate of viral replication or in the amount of viral components made after infection of a cell by a virus. The change is preferably a decrease in rate or amount of replication, though inhibiting or interfering at one step of the replication pathway may lead to an increase in the precursors necessary for that step.

The presence in solution of the 3' terminal structure of the WNV genomic (plus strand) RNA [WNV 3' (+) SL RNA] was previously confirmed by RNase structure probing (47). Three RNA-protein complexes (RPCs) were detected by gel shift mobility assays performed with Baby Hamster Kidney cell (BHK) cytoplasmic extracts and the WNV 3' (−) SL (stem loop) RNA probe (3). The same pattern of RNA-protein complexes was observed when WNV-infected or uninfected BHK S100 cytoplasmic cell extracts were used, suggesting that the proteins in these complexes were cellular proteins. The results of UV-induced crosslinking and Northwestern blotting studies indicated that the molecular masses of the RNA binding proteins in these complexes were 52, 84, and 105 kDa (FIG. 7). The specificity of these RNA-protein interactions was demonstrated by competition gel mobility shift and competition UV-induced cross-linking assays (3). The p52 protein was identified as EF-1α (46).

The present invention comprises compositions that are effective in prohibiting or interfering with the interactions of host cell proteins, particularly p52, p84 and p105, that are involved in viral replication and particularly with the interactions of these proteins with the WNV 3' (+) SL RNA. Methods of assaying for such compositions comprise adding compositions to cells infected with WNV, or cell-free systems, and measuring the reduction in viral replication, compared to infected cells or cell-free systems without the composition. An embodiment of the invention comprises adding a composition comprising a nucleic acid fragment that mimics the 3' (+) SL RNA in an amount effective to inhibit or interfere with viral replication.

The presence in solution of the 3' terminal structure of the WNV minus-strand RNA [WNV 3' (−) SL RNA] was previously confirmed by RNase structure probing (37), and the sequence of the WNV 3' (−) SL RNA is provided as SEQ ID NO 3. Three RNA-protein complexes (RPCs) were detected by gel shift mobility assays performed with BHK cytoplasmic extracts and the WNV 3' (−) SL RNA probe (37). The same pattern of RNA-protein complexes was observed when WNV-infected or uninfected BHK S100 cytoplasmic cell extracts were used, suggesting that the proteins in these complexes were cellular proteins. UV-induced crosslinking studies indicated that the molecular masses of the RNA binding proteins in these complexes were 42, 50, 60, and 108 kDa (FIG. 7). The specificity of these RNA-protein interactions was demonstrated by competition gel mobility shift and competition UV-induced cross-linking assays (37). p42 has been identified as TIAR/TIA-1.

FIG. 7 is a schematic drawing showing the conserved structures and sequences in WNV RNAs and the cell proteins that bind specifically to the 3' terminal regions of these RNAs. Top line—the WNV genomic RNA; Bottom line—the complementary minus strand RNA; PK—pseudoknot; DB—dumbbell shaped RNA structures; cell proteins are indicated by circles. Competition gel mobility shift data suggest that p108 and p105 are the same protein.

The present invention comprises compositions that are effective in prohibiting or interfering with the interactions of host cell proteins, particularly p42 (TIAR/TIA-1), p50, p60, and p108, that are involved in viral replication and particularly with the interactions of these proteins with the WNV 3' (−) SL RNA. Methods of assaying for such compositions comprise adding compositions to cells infected with WNV, or cell-free systems, and measuring the reduction in viral replication, compared to infected cells or cell-free systems without the composition. An embodiment of the invention comprises adding a composition comprising a nucleic acid fragment that mimics the 3' (−) SL RNA in an amount effective to inhibit or interfere with viral replication.

An embodiment of the present invention comprises methods for identification of one of the WNV 3' (−) SL RNA-binding proteins, p42, as T-cell intracellular antigen-related (TIAR) protein. The closely related protein, T-cell intracellular antigen-1 (TIA-1), was also shown to bind specifically to the WNV 3' (−) SL RNA. Results from WNV growth studies in TIAR-knockout and TIA-1-knockout cells show these cell proteins are important in flavivirus replication. Such knockout cells are also useful in assays for determining compositions that are effective in inhibiting flavivirus replication. For example, viral infections in knock-out cells for particular host proteins are useful for confirming the effects of selected compositions that are specific for interfering with one or more host proteins involved in viral replication. An embodiment of an assay comprises infecting knock-out cells, for example, cells lacking TIAR, with WNV, adding the composition being tested to one set of cells and not adding the composition to the control set of cells, and comparing the viral replication in the set of knock-out cells with the composition to the control set. Initial comparisons would be made in infected cells that were normal for the protein lacking in the knock-out cells.

A method of the present invention comprises inhibiting replication of a virus, comprising, administering a composition capable of inhibiting at least one host cell protein needed for replication of a virus, preferable wherein the virus is a flavivirus, more preferably wherein the flavivirus is West Nile Virus. Methods include inhibition of at least on host cell, preferably wherein the at least one host cell protein is selected from the group consisting of TIAR/TIA-1, p 52, p84, p105, p108, p42, p 50, or p60. Compositions used in such methods include composition comprising a nucleic acid construct, and include nucleic acid constructs that mimic the 3' end of the negative strand nucleic acid of a flavivirus or that mimic the 3' end of the plus strand nucleic acid of a flavivirus. As used herein, mimicking a nucleic acid means having a nucleotide sequence that is identical to the nucleic acid or has sufficient sequence homology to the nucleic acid such that the mimicking nucleic acid has the same protein interactions or nucleic acid function as the original nucleic acid. Mimicking includes nucleic acid sequences or other molecules or synthetic materials that have the same structure as the original nucleic acid. The original nucleic acid, the one that is being mimicked, can be a fragment of a nucleic acid that includes the end nucleotides or any polynucleotide found between the ends. The original nucleic acid may comprise the sequence of known organisms, or have homology to known organism sequences, or may comprise derived sequences. For example, the nucleic acid sequence may be the sequence of a flavivirus, particularly West Nile Virus. The compositions may comprise a small organic molecule, antibody, peptide, peptoid, or polynucleotide.

Embodiments of the present invention comprise assays for determining compositions that are effective in inhibiting or interfering with viral replication. One assay for determining compositions that inhibit viral replication, comprise, a) adding a composition to cells infected with a virus, and b) comparing the change in viral replication to the cells of a) to control cells infected with the virus. The change in viral replication can be any measureable change the viral replication including, but not limited to, a change in the rate of replication of the virus or a change in the amount of viral components synthesized. One embodiment comprises assays that determine compositions that are effective in inhibiting flavivirus replication, particularly West Nile virus. Another embodiment comprisies assys wherein the cells are knockout cells, such as the cells described herein. Knockout cells can comprise cells lacking one or more nucleic acid sequences or proteins, particularly host cell proteins including but not limited to, TIAR/TIA-1, p 52, p84, p105, p108, p42, p 50, or p60.

Methods of the present invention also comprise methods for treating a viral infection, comprising, administering to a human or animal having a viral infection, a composition that alters the interaction of one or more host cell proteins with a viral nucleic acid in an amount effective to inhibit or interfere with viral replication. The compositions comprise those taught herein, including but not limited to, a nucleic acid construct, a small molecule, an antibody, a peptide, peptoid or polynucleotide. The host cell proteins effected include but are not limited to, TIAR/TIA-1, p 52, p84, p105, p108, p42, p 50, or p60. Treatments include treatment of flaviviruses, particularly West Nile virus.

Using methods disclosed herein, p42, one of the four cell proteins previously reported to bind specifically to the WNV 3' (−) SL RNA, has been identified as TIAR/TIA-1. The methods can also be used to identify the other host cells involved in viral replication. It is the inventor's novel finding of the identification of a host protein that interacts specifically with the 3' SL of a flavivirus minus-strand RNA, the site of initiation for nascent genome RNA synthesis. TIA-1 and TIAR are closely related, multifunctional, RNA-binding proteins (20, 40) that have at least partial redundancy in their cellular functions (33). The data herein shows that the binding of TIAR to the WNV 3' (−) SL RNA is functionally important for viral replication.

TIAR and TIA-1 are evolutionarily conserved proteins; homologs in different mammalian species share 96% (TIA-1) and 99% (TIAR) identity (1), while homologs in divergent species such as *Drosophila* (6, 23) and *Caenorhabditis elegans* (44) each share about 46% amino acid identity with human TIA-1 and TIAR. Because flaviviruses replicate efficiently in a large number of divergent host species and cycle between invertebrate and vertebrate hosts during their natural transmission cycles, it is expected that these viruses would need to interact with evolutionarily conserved cell proteins to replicate efficiently in different hosts. TIAR and TIA-1 proteins were initially discovered in T cells, hence their name, but have since been found to be expressed in good quantities in many tissues including brain, spleen and macrophages (1), which are sites of flaviviruses replication in vivo.

The present invention is not limited to inhibition or interference with just flavivirus replication, but contemplates the inhibition or interference of other viruses that use host proteins, particularly host proteins that bind to nucleic acids, more particularly host proteins that bind to viral RNAs, and are also not limited to interference or inhibition in any particular species of cells. Thus for example, for proteins that are conserved among species, compositions that are effective in inhibiting the activity of one or both TIAR or TIA-1 of one host species, such as human cells, are effective in inhibiting the replication of the viruses requiring TIAR or TIA-1 in other host species, such as birds or insects Both TIAR and TIA-1 shuttle between the nucleus and the cytoplasm in viable cells. Flaviviruses replicate exclusively in the cytoplasm. Interestingly, the level of TIAR in the cytoplasm of BHK cells is about 10 times higher than in several mouse embryofibroblast cell lines and WNV grows to about 10 times higher titers (peak titer of about $10^{7.5}$ PFU/ml) in BHK cells than in the mouse cell lines (peak titer of about $10^{6.5}$ PFU/ml).

In selection/amplification experiments with pools of randomized RNAs, both TIAR and TIA-1 bound with high affinity to RNAs that contained one or more short sequences of poly U with a dissociation constant of about $2 \times 10^{-8}$ M (15). Replacement of the Us in these RNAs with Cs eliminated the protein-RNA interaction. Although both proteins selected RNAs containing stretches of Us, the RNA sequences selected by TIA-1 were not identical to those selected by TIAR. The RNA recognition motif 2 (RRM2) domains in both proteins mediated specific binding to uridylate-rich RNAs. However, the presence of the other two RRM domains increased the affinity of the interaction of the proteins with the U-rich RNAs (15).

In the 3' NCR of the TNF-α mRNA, a large fragment of AU-rich sequence containing clustered AUUUA pentamers was required for TIAR/TIA-1 binding (18, 33). The data presented here indicate that both TIAR and TIA-1 can also bind specifically to the WNV 3' (−) SL RNA and that the RRM2 domain mediates this interaction. Since poly U competed efficiently with the WNV 3' (−) SL RNA in the competition gel-mobility shift assays (FIG. 3), it is expected that the viral sequence(s) recognized by TIAR and TIA-1 contains Us. Although the WNV 3' (−) SL RNA is not AU-rich, two of the single stranded loops in this structure contain the sequences, UAAU and UUAAU. These sequences are conserved in single stranded loops in the SLs of other mosquito borne flaviviruses. Mapping studies are underway to identify the individual nucleotides in the WNV 3' (−) RNA required for binding by each of these proteins.

The observed dissociation constant ($K_d$) for the interaction between TIAR RRM2 and the WNV 3' (−) SL RNA was $1.5 \times 10^{-8}$ M, which is similar to the $K_d$ reported for the interaction between TIAR and U-rich synthetic RNA sequences (and also for other functionally relevant RNA-protein interactions, such as the interaction between the cellular U1A protein and the U1-RNA) (19). Interestingly, the binding activity of TIA-1 ($K_d$ of $1 \times 10^{-7}$ M) for the WNV 3' (−) SL RNA was about 10 times lower than that of TIAR. Comparison of the RRM2 domain sequences of TIA-1 and TIAR indicate that they differ at eight amino acid residues and that TIAR also contains an eleven amino acid deletion at the beginning of RRM2 (1). The ten fold lower binding activity of TIA-1 for the WNV 3' (−) SL RNA would be expected to result in TIAR out-competing TIA-1 for binding to the viral RNA affinity column and would reduce the likelihood of detecting unique TIA-1 peptides in the protein eluted from the viral RNA affinity column.

A number of cellular functions have been attributed to the RNA binding properties of TIA-1/TIAR. Both TIAR and TIA-1 regulate the generalized translational arrest that occurs following an environmental stress. Stress-induced phosphorylation of the translation initiation factor eIF-2α is followed by recruitment of poly (A)⁺ RNA into cytoplasmic stress granules by TIAR and TIA-1 (22). Stress granules and polysomes appear to be in equilibrium in cells (21). TIA-1/TIAR also function as specific translational silencers (18, 33). For example, TNF-α translation is blocked by the binding of TIAR and TIA-1 to specific U-rich sequences in the 3' NCR of this mRNA. Upon stimulation with lipopolysaccharides (LPS), this translational repression is overcome by the binding of an additional protein, p55, to the 3' NCR of the TNF-α mRNA (26). TIA-1 and TIAR have recently been shown to function as alternative splicing regulators by binding to specific U-rich intron (IAS1) sequences adjacent to cryptic 5' splice sites and enhancing the use of these 5' splice sites (14, 25). Such intron sequences exist in a subset of pre-mRNAs, including those of TIA-1 and TIAR, and it is thought that both proteins can regulate their own expression at the level of splicing as well as the expression of some other proteins (16). The yeast protein, Nam8p, a component of the U1 snRNP, is distantly related to TIA-1 and TIAR. It is interesting to note that even though the majority of the known cellular functions of TIAR and TIA-1 involve interactions with cellular mRNAs, it is the 3' terminal region of the WNV minus strand, not the positive strand genome, that interacts with these proteins.

Although both TIAR and TIA-1 have previously been implicated as effectors of apoptotic cell death, the specific roles of these proteins in apoptosis have not as yet been delineated. Introduction of purified TIAR or TIA-1 into the cytoplasm of thymocytes permeabilized with digitonin resulted in fragmentation of genomic DNA into nucleosome-sized oligomers (20, 40). Increased amounts of TIAR were translocated from the nucleus to the cytoplasm in response to exogenous triggers of apoptosis (39). TIA-1 was shown to be phosphorylated by a serine/threonine kinase activated during Fas-mediated apoptosis (41). Although not rigorously tested, no evidence of apoptosis was observed when rodent cells infected with WNV were examined at intervals up to 32 hr post infection after fixation and nuclear staining with Hoerchst dye (data not shown). A study with WNV indicated that apoptosis occurred by 72 hr in infected human mononuclear (K562) cells and mouse neuroblastoma (Neuro 2a) cells via the BAX pathway (32).

Both TIAR and TIA-1 appear to play important roles in embryo development. However, the specific functions of these proteins during development are not known. It was not possible to produce double knock-out mice because of lethality prior to embryonic day 8 (Kedersha and Anderson, unpublished data).

Interestingly, of the five types of the viruses tested in the TIAR and TIA-1 knock-out cells, only the growth of the flavivirus, WNV, was decreased in cells lacking TIAR. In contrast, the growth of the four other types of viruses was more efficient in one or both types of knock-out cells as compared to that in wild type cells. These data suggest that in the wild type cells, one or both of these proteins have a negative effect on the production of these viruses. However, the negative effect that the loss of TIAR and to a lesser extent the loss of TIA-1 have on WNV replication suggests that these proteins provide a necessary function for WNV during its replication cycle.

Though not wishing to be bound by any particular theory, one possible explanation for why the growth of WNV was not reduced to a greater extent in TIAR-knockout cells could be that the TIA-1 protein, which is present in increased amounts in the TIAR-knockout cells (FIG. 6), can substitute for TIAR by providing the function needed by the WNV. However, WNV replication in cells lacking TIAR was never as efficient as when TIAR was present. Also, although the efficiency of virus replication increased when TIAR-knockout cells were reconstituted with vector expressed TIAR (FIGS. 5 and 6), neither the amount of TIAR nor WNV replication reached wild type levels in these reconstituted cells.

The only known function of the flavivirus minus strand RNA is as a template for the synthesis of nascent genomic RNA. Specific binding of TIA-1/TIAR to the 3' terminus of the viral minus strand RNA template appears to play a positive role in virus replication. Possible functions of this interaction include assisting in the formation or stabilization the 3' terminal (−) SL and/or in the recognition of the minus template by the polymerase.

Whether the ability of TIA-1/TIAR to associate with stress granules is utilized by flaviviruses and/or the other types of viruses tested is not known. Flavivirus infections do not shut off host cell translation (27) and flaviviral nonstructural proteins and dsRNA (indicative of viral replication intermediates) have been co-localized to redistributed endoplasmic reticulum, trans-Golgi and intermediate compartment membranes (29, 30). Nevertheless, further studies are needed to investigate whether stress granules are present in flavivirus infected cells and if so, whether they are associated with viral replication complexes. If the binding of TIA-1/TIAR to viral minus strand RNAs in replicative intermediates results in their co-localization with stress granules, this would provide an environment in which the translation of growing nascent viral plus strand RNAs would be inhibited. Alternatively, the binding of TIA-1/TIAR by the viral RNA could keep it from caring out its normal cell functions during stress.

Though not wishing to be bound by any particular theory, it is believed that TIAR/TIA-1 may have several roles in viral replication, one role is in enhancing WNV replication by acting as transcription factors for plus strand synthesis. Another role involves stress granule formation. TIAR/TIA-1 form compartments much like stress granules that sequester viral plus strand RNA synthesis, so that translation of nascent plus strands into protein is inhibited. Another function is the inhibition of formation of stress granules by the cell in response to infection by a virus, which would prevent the shut off of cell protein translation and lead to a delay in the onset of apoptosis in the cells. Interference with the activity of TIAR/TIA-1 by the compositions of the present invention results in decreased synthesis of genome RNA, results in the shut off of cell protein synthesis and leads to the onset of apoptosis. The ability to affect the onset of apoptosis or to delay apoptosis can be applied to many disease states and treatments of such diseases by providing compositions that are effective in delaying or initiating apoptosis are contemplated by the present invention.

Compositions contemplated by the present invention include compounds capable of inhibiting viral replication, preferably by inhibiting the activity of host cell proteins involved in viral replication. Such compounds are capable of inhibiting the activity of host cell proteins in vitro and in vivo and show antiviral activity both in vitro and in vivo. In addition, the compositions of the present invention are capable of inhibiting the activity of host cell proteins without detrimentally affecting cellular viability.

One aspect of the present invention comprises administration of compositions comprising compounds such as nucleic acid constructs. For example, a nucleic acid construct can be a DNA molecule that is transcribed by the host cells to form decoy RNA molecules. The decoy RNA molecules then compete with the binding of host proteins, for example TIAR/TIA-1, to viral 3' RNA. Other preferred compounds include RNA molecules, small organic molecules, antibodies, peptides, peptoid, or polynucleotides that interfere with the binding of host proteins, for example TIAR/TIA-1, to the viral 3' RNA. An alternative method of administration comprises administration of compositions of decoy RNA made in vitro. Routes of administration comprise those known in the art, though preferably such compositions are delivered via injection or intranasal methods. Preferably, the decoy RNA comprises modified ribonucleic acid nucleosides that provide stability and resistance to nucleases. For example, 2-O-methyl RNA is very stable and is readily taken up by cells and is used for clinical applications. The present invention contemplates this and other modified RNAs.

Compositions for inhibiting the activity of host cell proteins such as p50, p60, p108, p105, p 52, p84, TIAR or TIA-1 can be provided as pharmaceutically acceptable formulations using formulation methods known to those of ordinary skill in the art. These formulations can be administered by standard routes. In general, the compositions may be administered by the topical, transdermal, oral, rectal or parenteral (e.g., intravenous, subcutaneous or intramuscular) route. In addition, the compositions may be incorporated into biodegradable polymers allowing for sustained release of the compound, the polymers being implanted in the vicinity of where drug delivery is desired, for example, in infected tissues or provided to the organism for sustained release of the compound to the entire organism, for example, via gastrointestinal absorption.

The dosage of the compound will depend on the condition being treated and the extent of infection, the particular compound, and other clinical factors such as weight and condition of the human or animal and the route of administration of the compound. It is to be understood that the present invention has application for human, veterinary or plant use. For example, for administration to humans, a dosage of between approximately 0.1-75 mg/kg/day, preferably, a dosage of between approximately 10-50 mg/kg/day, most preferably, a dosage of between approximately 10-30 mg/kg/day. Alternatively, nucleic acid constructs provided in methods of gene therapy are provided in dosages of picogram to micrograms/kg/day, between approximately 0.001 µg/kg/day to 100 µg/kg/day. Depending on the route of administration, the compound administered and the toxicity of that compound, a preferable dosage would be one that would yield an adequate blood level or tissue fluid level in the human, animal or insect that would effectively inhibit replication of the virus.

The formulations include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations suitable for nasal administration, wherein the carrier is a solid, include a coarse powder having an appropriate particle size, microns, which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

The compositions of the present invention are used in methods of treatment of viral diseases. Such methods comprise administration of a composition effective in interfering or inhibiting viral replication in an individual having a viral infection. Such compositions include compounds that are effective in interfering or inhibiting the interactions of host proteins in the viral replication pathway. In particular, such compositions interfere with the interactions by one or more of p 50, p 60, p108, p105, p 52, p84, TIAR or TIA-1 with viral nucleotides or alter other functions of the proteins, such as stress granule formation or apoptosis. An embodiment of a composition comprises a nucleic acid construct that mimics a portion of a viral nucleic acid, such that the nucleic acid construct, and competes for the binding of one or more host cell proteins, such as p 50, p 60, p108, p105, p 52, p84, TIAR or TIA-1. An embodiment of a method of treatment of a viral disease comprises administering to a human, animal or insect a composition comprising a nucleic acid construct capable of competing for binding of one or more host cell proteins related to viral replication, in an amount effective to inhibit viral replication. An embodiment of a method of treatment of West Nile virus infection comprises administering to an individual, including a human or an animal, infected with West Nile virus, a composition comprising a compound capable of affecting one or more host cell proteins involved in West Nile virus replication, in an amount effective to interfere with or inhibit viral replication.

As used herein, individual can mean humans, animals, birds, insects, plants or other organisms that can be infected by viruses.

As used herein, "a" or "an" can mean multiples. For example, "a cell" can mean at least one cell or more than one cell.

It should be understood, of course, that the foregoing relates only to preferred embodiments of the present invention and that numerous modifications or alterations may be made therein without departing from the spirit and the scope of the invention as set forth in the Examples and appended claims.

EXAMPLES

Example 1

Materials and Methods Used Herein

CELLS. Baby hamster kidney (BHK-21/W12) cells (42) (referred to hereafter as BHK cells) were used to prepare S100 cytoplasmic extracts or ribosomal salt wash cell extracts. BHK, CV-1 and Vero cells were maintained at 37° C. in a $CO_2$ incubator in Minimal Essential Medium (MEM) supplemented with 10 μg/ml gentamycin and 5% or 10% fetal calf serum (FCS).

TIAR-knockout C57BL/6 mice and TIA-1-knockout Balb/C mice were prepared as described previously (2, 33). Embryo fibroblast cell lines were established from wild type (W4 and TIA$^{+/+}$43), TIAR-knockout (NaR4 and TIAR$^{-/-}$43) and TIA-1-knockout (a$^{-/-}$43 and TIA$^{-/-}$44) mouse embryos using the standard NIH 3T3 protocol.

To prepare control-reconstituted and TIAR-reconstituted (TIAR-REC) cell lines, TIAR-knockout (TIAR-$^{-/-}$43) cells were transfected with a pSR-α-hygromycin vector containing full-length human TIAR cDNA (a gift from Dr. M. Streuli, Dana Farber Cancer Institute, Boston, Mass.) by the calcium phosphate method (35). Stable cell lines were established from clones that grew in the presence of hygromycin. Reconstituted cells were re-selected by growth in hygromycin for one week prior to use in experiments. These cell lines were maintained in MEM supplemented with 10% FCS, 10 mM HEPES and 10 μg/ml gentamycin in a $CO_2$ atmosphere at 37° C.

VIRUSES. Stocks of WNV, strain EG101, (titer=$2 \times 10^8$ PFU/ml) and Sindbis virus, strain SAAR 339, (titer=$7 \times 10^9$ PFU/ml) were prepared as 10% (w/v) newborn mouse brain homogenates. A stock of vaccinia virus, Wyeth strain, was prepared as a CV-1 cell lysate (titer=$1.2 \times 10^8$ PFU/ml). A stock of herpes simplex virus [HSV-1; strain H129 (H1)], was prepared as a media pool in Vero cells (titer=$1.6 \times 10^8$ PFU/ml) and vesicular stomatitis virus (VSV), strain Indiana, was prepared as a media pool in L cells (titer=$4.8 \times 10^7$ PFU/ml).

For virus growth experiments, confluent monolayers of wild-type or knockout cells in T25 flasks were infected with WNV at a multiplicity of infection (MOI) of 1, and culture fluid samples (0.5 ml) were harvested at different times post-infection (p.i.). At each time point, 0.5 ml of fresh media was replaced to maintain a constant volume in the flask. Harvested WNV samples were titrated in duplicate on BHK cells by plaque assay. Monolayers of cells in T25 flasks were also infected at an MOI of 1 with Sindbis virus, vaccinia virus, herpes simplex virus (HSV)-1, or vesicular stomatitis virus (VSV). Virus yields at different times post-infection were determined by plaque assay. Sindbis was plaqued on BHK cells, vaccinia on CV-1 cells, HSV-1 on Vero cells, and VSV on BHK cells.

IN VITRO TRANSCRIPTION OF $^{32}$P-LABELED RNA PROBES AND UNLABELED RNA TRANSCRIPTS. Plasmid p75nt(−)3' was previously constructed by P.-Y. Shi (36). A PCR product, PCRT73' (−)SL, that consisted of the 75 3' terminal nts of the WNV minus-strand RNA (SEQ ID NO 3) with three extra C's at the 5' end copied from the T7 promoter, was amplified from plasmid p75nt(−)3' DNA using a M13 reverse primer (5'-CAGGAAACAGCTATGAC-CATG-3'), and a forward primer (5'-AGTAGTTCGCCTGT-GTGAGC-3'). The 3' (−)SL RNA was transcribed from the amplified PCR DNA. The T7 polymerase used for in vitro RNA transcription was expressed from BL21 cells containing pAR1219 (kindly provided by Dr. F. W. Studier, Brookhaven National Laboratory) and purified as described by Davanloo et al. (11).

The methods used for in vitro transcription and gel purification of the $^{32}$P-labeled RNA probes and unlabeled competitor RNAs were described previously (37). Large scale batches of unlabeled RNAs, needed for RNA affinity columns, were prepared by scaling up the in vitro transcription reaction to 1 ml and extending the reaction time to 4 h.

RNA-AFFINITY COLUMN. In vitro transcribed WNV 3' (−)SL RNA was oxidized with periodate in the presence of NaOAc (pH 5) and then attached to an agarose adipic acid matrix as described by Blyn et al. (4, 5). The RNA-matrix (1 ml) was poured into a 10 ml column and then equilibrated with column binding buffer [5 mM HEPES (pH 7.5), 25 mM KCl, 2 mM $MgCl_2$, 0.1 mM EDTA, and 2 mM dithiothreitol].

BHK S100 cell extracts prepared as described previously (37) were subjected to ammonium sulfate precipitation prior to passage through an RNA-affinity column. Ammonium sulfate was first added to a final concentration of 16%. Ammonium sulfate was then added to the supernatant obtained from the first precipitation to a final concentration of 45% and the resulting pellet was resuspended in storage buffer. The pellet fraction was preincubated with non-specific competitors polyIC (1 mg/ml) and heparin (500 µg/ml) at 4° C. for 10 min, and then passed over the RNA-affinity column three to five times. The column was then washed several times with column binding buffer and once with the same buffer containing 0.2 M NaCl. The bound proteins were eluted with column binding buffer containing 1 or 2 M NaCl. The eluted fractions were subjected to buffer exchange in a Centricon-30 (Amicon). Aliquots of each fraction were analyzed for RNA binding activity by gel mobility shift assay. Proteins were detected by Gold blot staining (Integrated Separation Systems). The proteins in the eluted fractions were then separated by SDS-PAGE, visualized by Coomassie blue staining. Protein bands were excised and peptides were generated by trypsin digestion. The peptides were separated by HPLC and the sequences of selected peptides were determined by automated liquid chromatography-tandem mass spectrometry using a Finnigan MAT LCQ ion trap mass spectrometer as described previously (12, 13, 38).

RNA-PROTEIN INTERACTION ASSAYS. Gel mobility shift and UV-induced crosslinking assays were performed as described previously (37). Prior to use in these assays, RNA probes were denatured by incubation at 90° C. for 10 min followed by renaturation by slow cooling to 60° C. and incubation at 60° C. for ~2 min. The probe was then kept on ice until use.

IMMUNOPRECIPITATION OF UV-CROSSLINKED PROTEINS. Proteins in S100 cytoplasmic extracts were first crosslinked to $^{32}$P-labeled WNV 3' (−)SL RNA as described above. The cross-linked proteins were then incubated for 2 h at 4° C. with 1 µg/ml of anti-TIAR antibody [6E3, murine mAb IgG2a; (1)] or anti-TIA-1 antibody [ML29, murine mAb IgG1; (22, 39)] that had been preincubated with Sepharose A CL-4B beads (Pharmacia). The precipitated complexes were pelleted by centrifugation at 300×g, washed twice with dilution buffer [0.1% Triton X-100 and 0.5% nonfat dry milk in TSA buffer (0.01 M Tris-HCl, pH 8.0, 0.14 M NaCl, 0.025% NaN$_3$)], once with TSA buffer and once with 0.05 M Tris-HCl (pH 6.8). The immunoprecipitated complexes were then separated by 10% SDS-PAGE and visualized by autoradiography.

IMMUNOBLOTTING. BHK cells from a confluent monolayer in a T75 flask were trypsinized, pelleted by centrifugation for 3 min at 150×g, and washed three times with 1×phosphate-buffered saline (PBS). The cell pellet was resuspended in ice-cold lysis buffer (1×PBS, 1% Nonidet P-40, 0.5% sodium deoxycholate, 0.1% SDS) containing freshly added protease inhibitors (1×Complete, Roche), and passed through a 21-gauge needle four times. Nuclei were removed from the cytoplasmic extracts by centrifugation at 10,000×g for 10 min at 4° C. The total protein concentration in the extracts was determined using a Dc protein assay kit (BioRad). Proteins in 20 µg of extract were separated by 10% SDS-PAGE and then electrophoretically transferred to a nitrocellulose membrane (0.45 micron pore size, BioRad). The membrane was blocked with Blotto A [10 mM Tris-HCl, pH 8.0, 150 mM NaCl (TBS), 5% non-fat dry milk, 0.05% Tween 20] for 1 hr at room temperature or overnight at 4° C., and probed first with an anti-protein primary antibody and then with a horseradish peroxidase (HRP)-conjugated secondary antibody diluted in Blotto A. The membrane was washed three times with 1×TTBS (1×TBS containing 0.05% Tween 20) and then once with 1×TBS prior to incubation with Chemiluminescence Reagent (Santa Cruz Biotech) and detection of the proteins by autoradiography.

Mouse anti-TIAR monoclonal antibody 6E3 was used at 0.8 µg/ml and goat anti-TIA-1 polyclonal antibody (Santa Cruz Biotech) was used at 0.5 µg/ml. HRP-conjugated goat anti-mouse IgG and donkey anti-goat IgG were used at 0.2 µg/ml (Santa Cruz Biotech).

INDIRECT IMMUNOFLUORESCENCE. Cells were grown to about 50% confluency in the wells of a two-chamber Lab-Tek II slide (Nalge Nunc International) and infected with WNV at a MOI of 5. At various times after infection, the cells were fixed with 2% paraformaldehyde for 10 min at room temperature, permeabilized with ice-cold methanol for 10 min, stained with a 1:100 dilution of a hyperimmune mouse anti-WNV antibody (Walter Reed Army Institute of Research) for 1 h, and then washed three times with PBS. The cell nuclei were then stained with Hoechst Dye (33258) and FITC-goat anti-mouse IgG (Jackson ImmunoResearch Laboratories) for 1 h and washed three times with PBS. The coverslips were mounted in vinol mounting media (17) and viewed with a Nikon Eclipse 800 microscope equipped with epifluorescence optics and appropriate filters for detection of FITC, Texas red or Hoechst dye.

PREPARATION OF FIGURES. Autoradiographs of gels or membranes were scanned with an Arcus II Agfa scanner. The digitalized images were adjusted using Adobe Photoshop (version 5.5) software on a Power PC Macintosh G3.

Example 2

Purification of the WNV 3' (−) SL RNA-Binding Protiens

Three RNA-protein complexes, RPC1, -2 and -3, were detected in gel mobility shift assays done with a $^{32}$P-WNV 3'(−) SL RNA probe and BHK S100 extracts (37). UV-induced crosslinking assays indicated that these complexes contained four cell proteins (p42, p50, p60, and p108) that bound specifically to the WNV 3' (−) SL RNA. An RNA affinity column was used to purify these viral RNA binding proteins.

In a preliminary experiment, a BHK S100 cytoplasmic extract that was prepared from ten T150 flasks of cells was subjected to precipitation with different concentrations of ammonium sulfate. Supernatant and pellet fractions were analyzed for viral RNA binding activity by gel mobility shift and UV-induced crosslinking assays. Although a pellet was obtained after precipitation with 16% ammonium sulfate, none of the four cell proteins that bound to the viral 3' RNA were present in this pellet in detectable amounts. After precipitation with 45% ammonium sulfate, there was good recovery of RPC2 and RPC3, but only a small amount of RPC1 were detected in the pellet fraction by gel mobility shift assay. UV-induced crosslinking assays indicated that p60, p50, p42, but only a small amount of p108, were present in the pellet fraction.

The proteins in the 45% ammonium sulfate pellet were resuspended in column binding buffer, incubated with non-specific RNA competitors, and then passed through a WNV 3' (−) SL RNA affinity column several times (4, 5). The column was washed and the bound proteins eluted. Each eluted fraction was concentrated with a Centricon-30 and assayed for viral RNA binding activity by gel-mobility shift and UV-induced cross-linking assays. FIG. 1 shows the analysis of WNV 3'(−) SL RNA-binding proteins in fractions eluted from an agarose-adipic acid hydrazide RNA affinity column. FIG. 1-A, Gel-shift assays, Lane 1, free probe: lane 2, final flow-through fraction from the RNA-affinity column; lane 3, first binding buffer wash fraction; lane 4, 0.2 M NaCl wash fraction; lanes 5 and 6, fractions eluted with 1 or 2 M NaCl respectively; lanes 7 and 8, fractions eluted from a "beads-only" control column with 1 or 2 M NaCl, respectively. For each of the fractions, 1 μl of a total of 100 μl was analyzed on the gel. The positions of the three RPCs are indicated by arrows. B. Coomassie blue staining of the eluted fractions from an agarose-adipic acid hydrazide RNA affinity column. Lane 1, aliquot of sample loaded on the affinity column (10 μl of 3 ml); lane 2, fraction eluted with 2 M NaCl from a "beads only" a control column (30 μl of 100 μl); lane 3, fraction eluted with 2 M NaCl from the RNA-affinity column (30 μl of 100 μl). The positions of the eluted proteins are indicated by arrows. The protein markers are shown on the left side of the gel. M, multimer of the probe; fp, free probe.

Figure 1B:
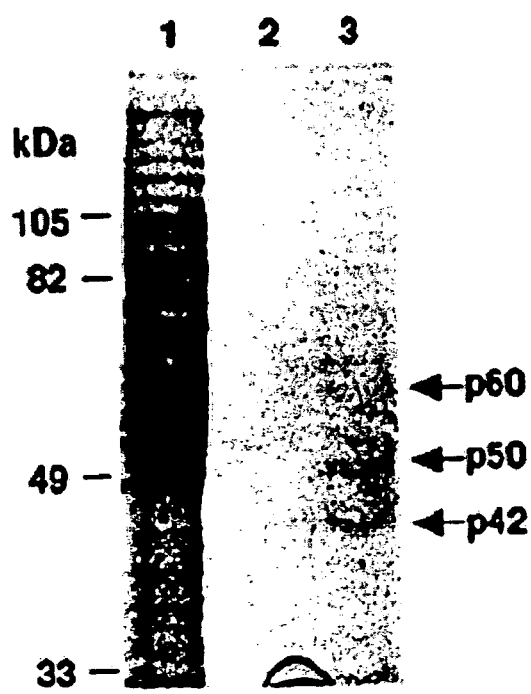

Little or no specific binding activity was detected in the flow-through fraction by gel-mobility shift assay (FIG. 1A, lane 2) or in the wash fractions (FIG. 1A, lanes 3 and 4). The majority of the RNA binding activity was eluted with 2 M NaCl (FIG. 1A, lane 6). Proteins in aliquot of the eluate was separated by 10% SDS-PAGE, transferred to a nitrocellulose membrane and stained with GoldBlot. Bands with molecular masses similar to those of three of the expected proteins (p60, p50 and p42), as well as some background bands were observed (data not shown). The p42 band was clearly the strongest band. The remainder of the eluted protein was then electrophoresed on one lane of a 10% SDS-PAG and then stained with Coomassie blue (FIG. 1B, lane 3). The p42 and p50 bands were excised from the gel and peptides were generated by trypsin digestion. The peptides were separated by HPLC and the sequences of selected peptides were determined by automated liquid chromatography-tandem mass spectrometry (Beckman Research Institute of the City of Hope). Insufficient unique sequence for p50 was obtained to allow the identification of this protein. The sequences of four peptides obtained from p42 were identical to sequences found in both TIA-1 and TIAR, while the sequences of two additional p42 peptides were unique to TIAR. TIAR and TIA-1 are closely related RNA binding proteins that bind U-rich sequences interspersed with As (15). Both proteins contain three N-terminal RRM domains, each approximately 100 amino acids in length, and a C-terminal auxiliary domain of approximately 90 amino acids (1). TIAR and TIA-1 share 80% overall amino acid identity, with the highest degree of similarity in RRM domain 3 (91% identity) and the lowest degree of similarity (about 50% identity) in the C-terminal auxiliary domain. The data suggest that p42 is TIAR. However, because of the high degree of sequence homology between TIAR and TIA-1, the possibility that TIA-1 also binds specifically to the WNV 3' (−) SL RNA could not be ruled out.

Studies to identify the other three cell proteins that bind to the WNV 3' (−) RNA are in progress. Previous preliminary studies showed that neither anti-EF-1α nor anti-La antibody produced a supershift when added to S100 cytoplasmic extracts incubated with the WNV 3' (−) SL RNA probe (Li and Brinton, unpublished data).

Example 3

Confirmation that TIAR and TIA-1 Bind to the WNV 3' (−) RNA

Anti-TIAR (6E3) and anti-TIA-1 (ML-29) antibodies were used to immunoprecipitate UV-induced crosslinked WNV 3' (−) SL RNA-protein complexes from BHK S100 cytoplasmic extracts after treatment with RNase. Results from this experiments are shown in FIG. 2. BHK S100 cytoplasmic extracts from BHK cells were incubated with a $^{32}$P-labeled WNV 3'(−) SL RNA probe. The complexes were cross-linked by exposure to UV light, treated with RNase and then precipitated with anti-TIAR or anti-TIA-1 antibody. The precipitates were analyzed by 10% SDS-PAGE. Lane 1, anti-TIAR antibody was added; lane 2, anti-TIA-1 antibody was added; lane 3, free probe. The expected UV-induced cross-linked p42 product is indicated by an arrow. The protein markers are shown on the right side of the gel. Even though four cell proteins (p108, p60, p50, and p42) that crosslinked to the viral RNA probe were present in these extracts, only the anti-TIAR antibody precipitated the p42-WNV 3' (−) SL RNA complex (FIG. 2, lane 1). Anti-TIA-1 antibody also precipitated the p42-WNV 3' (−) SL RNA complex (FIG. 2, lane 2). However, the band obtained after immunoprecipitation with anti-TIA-1 antibody was not as strong as that seen with the anti-TIAR antibody. These data suggest that the p42 band detected in UV crosslinking experiments with S100 extracts contained both TIAR and TIA-1.

Example 4

Analysis of the Specification of the Viral RNA-Cell Protein Interactions

Purified GST-TIAR and GST TIA-1 fusion proteins (41) were tested for their ability to bind to the WNV 3' (−) SL RNA in a gel mobility shift assay. The results of preliminary experiments showed that at least a four times higher concentration of GST-TIA-1 was required to detect binding in gel mobility shift assays as compared to GST-TIAR (data not shown). Therefore, different concentrations of GST-TIA-1 (200 nM) and GST-TIAR (50 nM) were used for the representative competition gel shift assays shown in FIGS. 3A and B. Although the predominant gel shift band observed with both of the fusion proteins migrated to the middle of the gel, additional slower and faster migrating complexes were also observed. The slower migrating bands most likely contain aggregated complexes, since the density of these bands increased with increasing protein concentration (data not shown). The faster migrating bands most likely contained breakdown fragments that retained the RRM2 region containing the viral RNA binding site (see FIGS. 3, C and D).

FIG. 3 shows the analysis of the specificities of the interactions between the WNV 3'(−) SL RNA and the recombinant TIAR or TIA-1 proteins. FIG. 3-A. Competition gel-shift assays with a purified GST-TIA-1 fusion protein. Lane 1, free probe; lane 2, probe plus 200 nM of purified GST-TIA-1 fusion protein; lanes 3 to 14, probe plus 200 nM of purified GST-TIA-1 fusion protein and the indicated competitor RNA. FIG. 3-B. Competition gel shift assays with a purified GST-TIAR fusion protein. Lane 1, free probe; lane 2, probe plus 50 nM of purified GST-TIAR fusion protein; lanes 3 to 14, probe plus 50 nM of purified GST-TIAR fusion protein and the indicated competitor RNA. SC, specific competitor-unlabeled 75 nt WNV 3'(−) SL RNA (SEQ ID NO 3); M, multimer of the probe; fp, free probe. FIG. 3-C. Purified GST-fusion proteins (500 nM), each containing a single RRM domain of TIA-1, were analyzed by gel mobility shift assay. Lane 1, free probe; lane 2, probe plus the GST-TIA-1 RRM1; lane 3, probe plus the GST-TIA-1 RRM 2; lane 4, probe plus the GST-TIA-1 RRM3. M, multimer of the probe; fp, free probe. FIG. 3-D. Purified GST-fusion proteins (200 nM), each containing a single RRM domain of TIAR, were analyzed by gel mobility shift assay. Lane 1, free probe; lane 2, probe plus the GST-TIAR RRM1; lane 3, probe plus the GST-TIAR RRM2; lane 4, probe plus the GST-TIAR RRM3.

Figure 3A:
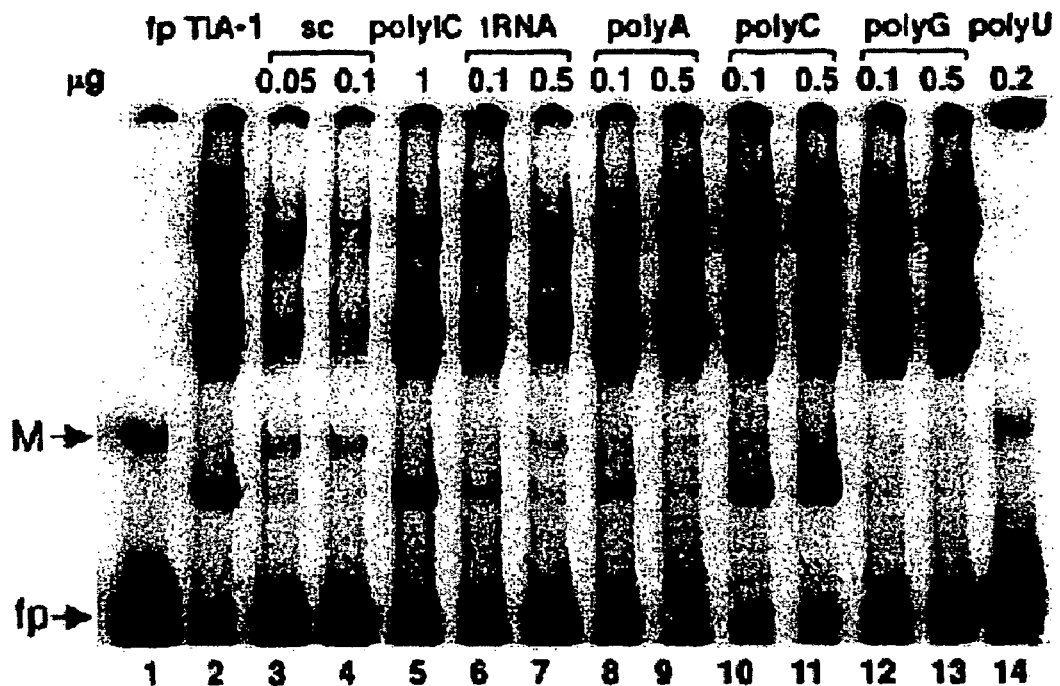
Figure 3B:
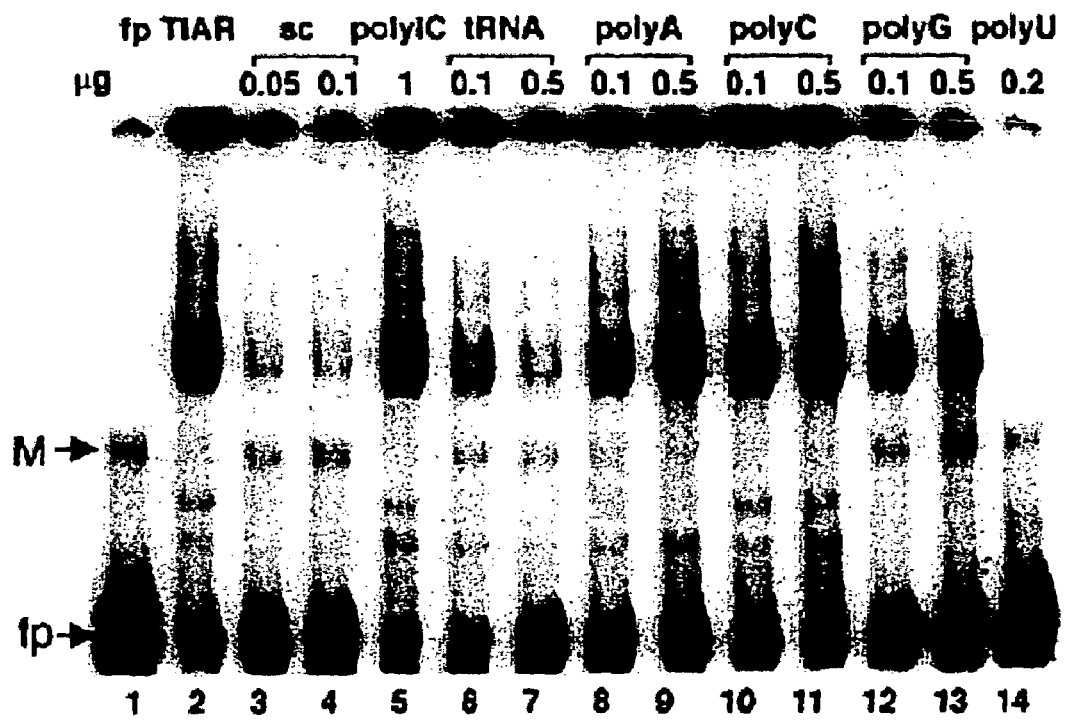
Figure 3C:
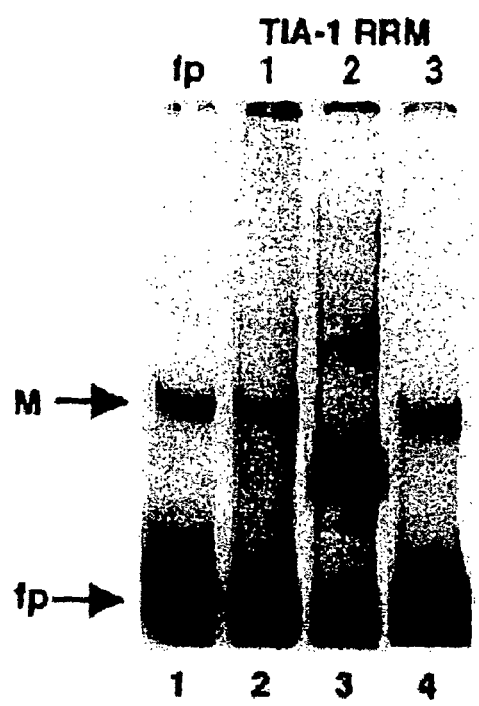
Figure 3D:
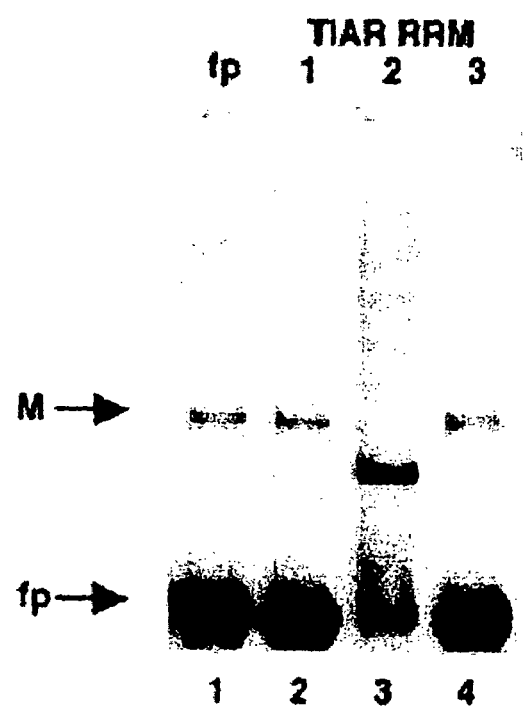

Unlabeled WNV 3' (−) SL RNA (50 or 100 ng) was used as the specific competitor and competed efficiently with the labeled probe (FIG. 3A, lanes 3 and 4; FIG. 3B, lanes 3 and 4). The nonspecific competitors, poly (IC), poly (A), poly (G), and poly (C), showed little or no competition even at concentrations of 500 ng or 1 μg (FIGS. 3, A and B). tRNA (100 or 500 ng) partially competed, but with a lower efficiency than the specific competitor (FIG. 3A, lanes 6 and 7 and FIG. 3B, lanes 6 and 7). As expected from previous studies showing that TIAR and TIA-1 bound to U rich sequences (1), poly U competed efficiently (FIG. 3A, lane 14 and FIG. 3B, lane 14). These data indicate that both the GST-TIAR and GST-TIA-1 proteins bind specifically to the WNV 3' (−) SL RNA.

TIA-1 and TIAR each contain three RRM domains. To determine whether one of these RRM domains contains the major binding site for the WNV 3' (−) SL RNA, purified truncated GST fusion proteins, GST-TIA-1 RRM1, GST-TIA-1 RRM2, and GST-TIA-1 RRM3 (FIG. 3C, lanes 2 to 4), and GST-TIAR RRM1, GST-TIAR RRM2, GST-TIAR RRM3 (FIG. 3D, lanes 2 to 4), were tested for their ability to bind to the WNV 3' (−) SL RNA in gel mobility shift assays. Only the GST-TIA-1 RRM2 (FIG. 3C, lane 3) and the GST-TIAR RRM2 (FIG. 3D, lane 3) were able to bind the WNV 3' (−) SL RNA. These data suggest that the major WNV 3' (−) SL RNA binding site in both TIAR and TIA-1 is RRM 2.

Example 5

Determination of the Relative Dissociation Constants ($K_D$) for the Viral RNA-Cell Protein Interactions FIG. 4 shows quantification of the protein-RNA interactions. FIG. 4-A shows a representative gel mobility shift assay done with increasing amounts of the GST-TIA-1 RRM2 protein and a constant amount of WNV 3'(−) SL RNA. Lane 1, free probe; lanes 2 to 9, probe plus the GST-TIA-1 RRM2 in the amounts indicated. M, multimer of the probe; fp, free probe. FIG. 4-B. The percent $^{32}$P-WNV 3'(−) SL RNA bound was plotted against the concentration of TIA-1 to generate a theoretical saturation binding curve. Inset, the data from the saturation binding curve were transformed as described previously (28, 43). The stoichiometry of the interaction of TIA-1 with the WNV 3'(−) SL RNA, as determined by the slope of the line in the inset graph, was about 1:1. The dissociation constant was calculated using the equation log (% bound/% unbound)+2=n{ log [TIA-1(nM)] +1 }−log $K_d$. The Kd was estimated to be 112 nM for TIA-1. FIG. 4-C. A representative gel mobility shift assay done with increasing amounts of the GST-TIAR RRM2 protein and a constant amount of WNV 3'(−) SL RNA. Lane 1, free probe; lanes 2 to 9, probe plus the GST-TIAR RRM2 in the amounts indicated. FIG. 5-D. The percent $^{32}$P-WNV 3'(−) SL RNA bound was plotted against the concentration of TIAR to generate a theoretical saturation binding curve. Inset, the data from the saturation binding curve were transformed. The Kd was estimated to be 15 nM for TIAR. The stoichiometry of the interaction of TIAR with the WNV 3'(−) SL RNA, as determined by the slope of the line of the inset graph, was about 1:1. M, multiprobe; fp, free probe.

Figure 4A:
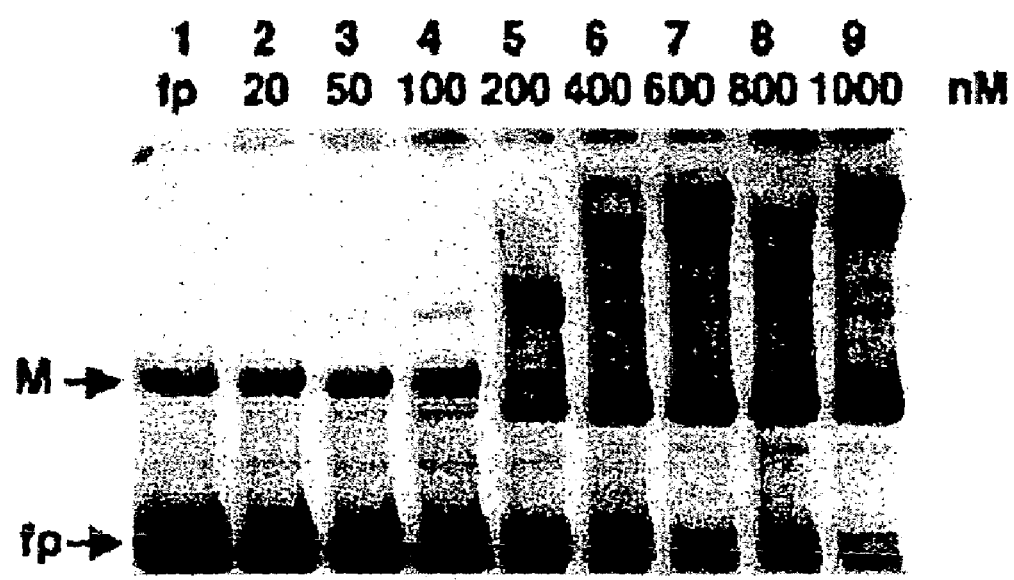
Figure 4B:
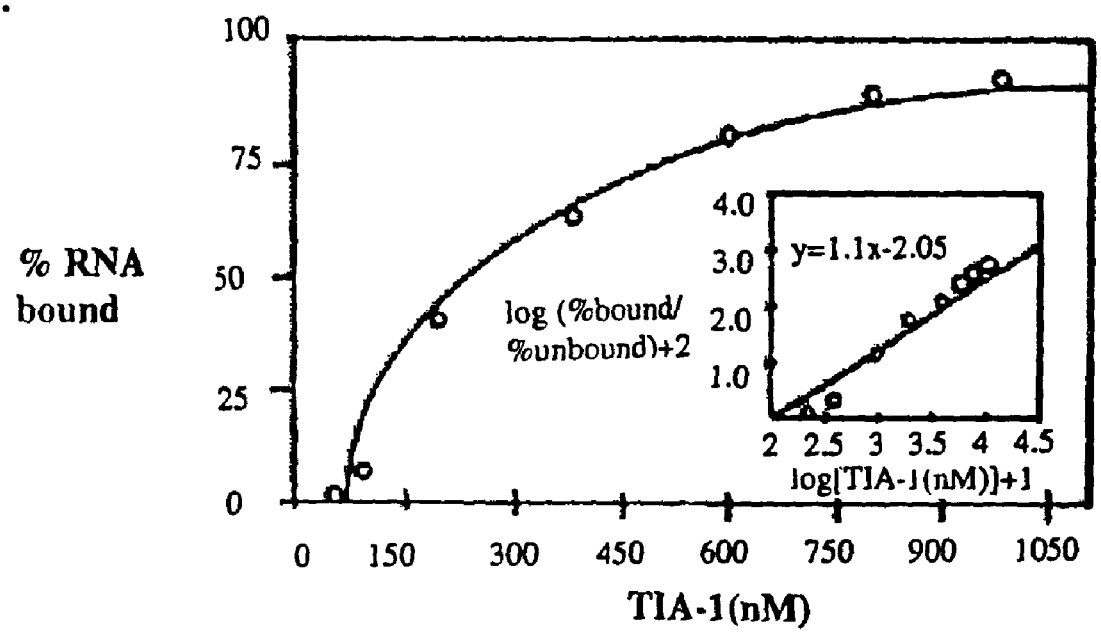
Figure 4C:
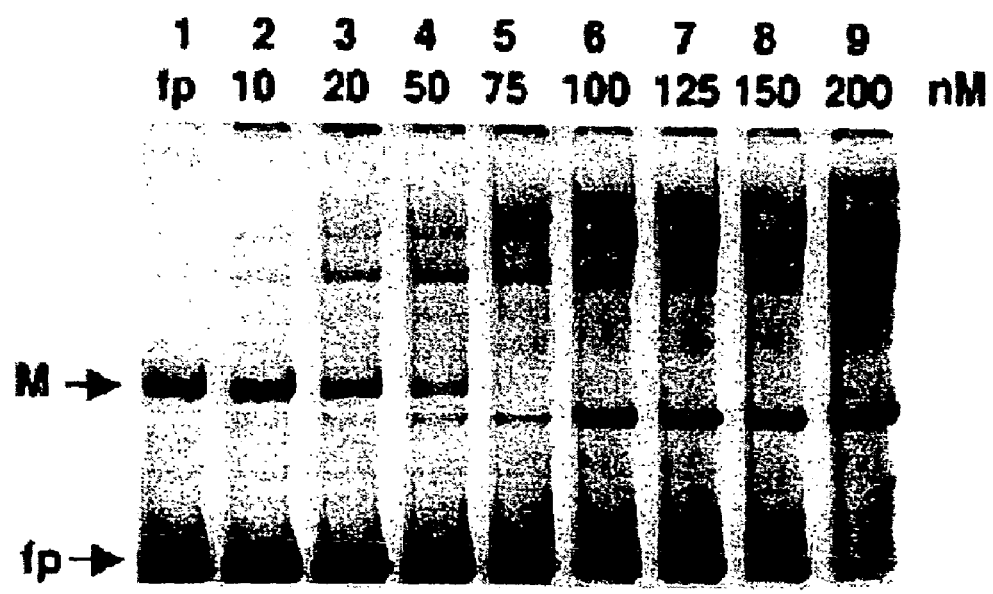
Figure 4D:
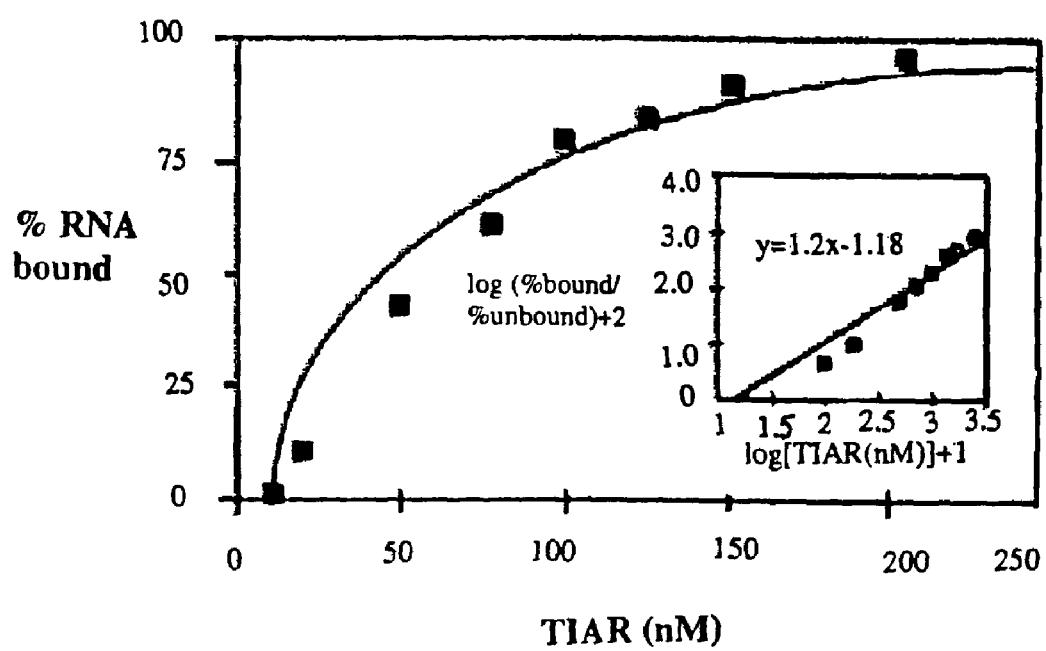

Gel mobility shift assays were performed using different amounts of GST-TIA-1 RRM2 or GST-TIAR RRM2 protein and a constant amount of the $^{32}$P-WNV 3' (−) SL RNA. Although gel shift bands were observed with 10 nM of GST-TIAR RRM2, bands for GST-TIA-1 RRM2 were first observed when 50 nM of protein were used (FIGS. 4A and 4C). A theoretical saturation binding curve was generated by plotting the percentage of bound WNV 3' (−) SL RNA versus the concentration of either GST-TIA-1 RRM2 or GST-TIAR RRM2. The data from the saturation binding curve were transformed as described previously (28, 43). The relative $K_d$ for the interaction between GST-TIA-1 RRM2 and the WNV 3' (−) SL RNA was estimated to be about $1.12 \times 10^{-7}$ M (FIG. 4A), while the relative $K_d$ for the interaction between GST-TIAR RRM2 and the WNV 3' (−) SL RNA was estimated to be about $1.5 \times 10^{-8}$ M (FIG. 4C). The slope (n) of the line represents the ratio of GST-TIA-1 RRM2 or GST-TIAR RRM2 molecules to WNV 3' (−)SL RNA molecules in each RNA-protein complex (FIGS. 4B and D, insets). For both proteins, the slope was calculated to be about 1 (1.1 for TIA-1 and 1.2 for TIAR), suggesting that approximately one TIAR or TIA-1 molecule binds to each WNV 3' (−) SL RNA molecule. Similar $K_d$ and n values were obtained from four independent experiments with standard deviations of ±15 nM and ±0.15 for GST-TIA-1 RRM2 and ±5 nM and ±0.1 for GST-TIAR RRM2, respectively. These data indicate that the relative binding activity of the TIAR-RRM2 for the WNV 3' (−) SL RNA is more than 10 times higher than that of the TIA-1-RRM2 for the same RNA. Although the RRM2 domain was shown to contain the main binding site for the viral RNA (FIG. 3), both proteins also contain two additional RRM domains that are likely to participate in stabilizing the RNA-protein interaction. The relative binding activities of the complete proteins for the viral 3' RNA therefore would be expected to be somewhat higher.

Example 6

Effect of TIAR and TIA-1 on the Replication of WNV

Figure 5A:
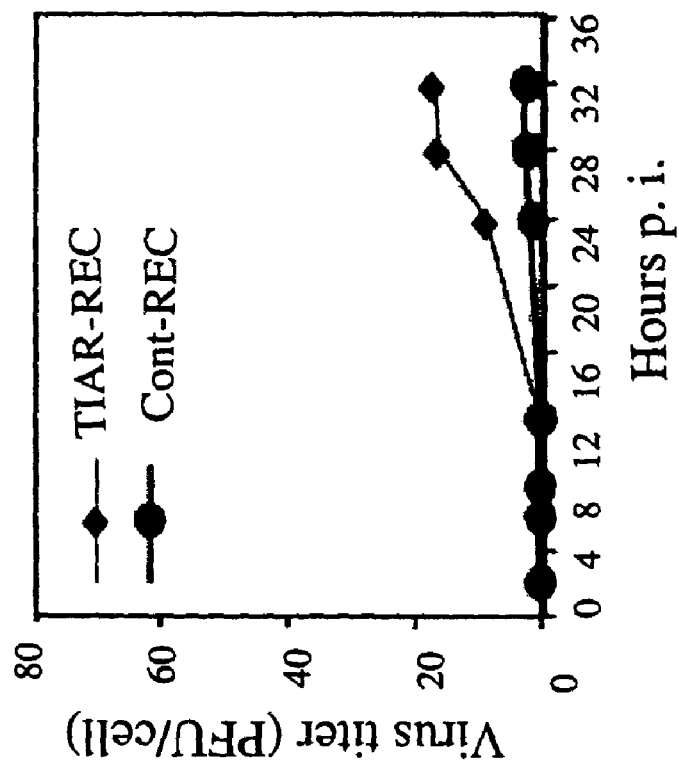

As one means of assessing the effect of the TIAR and TIA-1 proteins on WNV replication, virus growth was compared in TIAR-knockout, TIAR-reconstituted, TIA-1-knockout, and control murine embryo fibroblast cell lines. Confluent cell monolayers were infected with WNV at an MOI of 1. Culture fluid samples were taken at 2, 8, 12, 24, 28, and 32 hr postinfection (p.i.). A representative growth curve of WNV in wild type (W4), TIAR-knockout (NaR4), and TIA-1-knockout ($a^{-/-}43$) cells is shown in FIG. 5A. Virus titers were expressed as PFU/cell, because the various cell lines grew to different but characteristic densities when confluent. The peak titer of WNV produced by TIAR-knockout cells was significantly lower (6-8 fold) than that produced by control cells (FIG. 5A). WNV grew to comparable peak titers in TIA-1-knockout cells and control cells, but peak virus levels were not attained until 6 hr later in TIA-1-knockout cells. Similar results were obtained with an additional set of separately derived control and knockout cell lines (data not shown) suggesting that the decrease in WNV replication observed in the knockout cells was not due to a peculiarity of a single cell line.

The efficiency of infection of these cells with WNV was investigated by indirect fluorescence. Control, TIAR-knockout and TIA-1 knockout cells were infected with WNV for 24 h, 28 h, or 32 h, fixed, and then stained with Hoechst dye and anti-WNV antibody. At 24 hr post infection, bright virus-specific perinuclear staining was observed in about 40% of the control and TIA-1-knockout cells. However, the stained perinuclear areas in the infected control cells were generally wider than those in the TIA-1-knockout cells. Although a similar percentage of TIAR-knockout cells showed virus-specific perinuclear staining at 24 hr, the fluorescence in these cells was faint and the areas of staining were focal. The intensity of the perinuclear staining in the infected TIAR-knockout cells increased somewhat by 28 h post infection and thin perinuclear rings were observed in some cells. At 32 h, although the intensity and distribution of the fluorescence had increased in the WNV-infected TIAR-knockout cells, only about 10-20% of the cells contained broad, brightly stained perinuclear rings. These results suggest that WNV infects similar numbers of cells in the three types of cultures but that virus replication is most efficient in the control cells, slightly less efficient in the TIA-1-knockout cells and least efficient in the TIAR-knockout cells.

Example 7

Growth of Other Types of Viruses in TIAR-Knockout and TIA-1-Knockout Cells

To determine whether other types of viruses also showed reduced growth in TIAR-knockout cells, control, TIAR-knockout, and TIA-1-knockout cells were infected with Sindbis virus, vaccinia virus, VSV or HSV-1 at an MOI of 1. Sindbis virus is another plus strand RNA virus but from the alpha togavirus family. VSV, a rhabdovirus, is a minus strand RNA virus, while vaccinia, a poxvirus, is a DNA virus. Similar to WNV, these three viruses replicate in the cytoplasm of infected cells. HSV-1, a herpes virus, is a DNA virus that replicates in the nucleus. Culture fluid samples were harvested at the indicated times after infection and titered by plaque assay. Representative growth curves obtained for each of the viruses are shown in FIG. 5C through F. Confluent monolayers of control (W4), TIA-1-knockout ($a^{-/-}43$) and TIAR-knockout (NaR4) cells were infected with (A) WNV, (C) VSV, (D) Sindbis virus, (E) HSV-1, or (F) vaccinia virus at an MOI 1. Confluent monolayers of control (W4), TIAR-reconstituted (TIAR-Rec) or control reconstituted (Cont-Rec) cells were infected with (B) WNV at MOI 1. Culture fluid samples were taken at the indicated hours post-infection (p.i.) and titered by plaque assay.

Figures 6A, 6B:
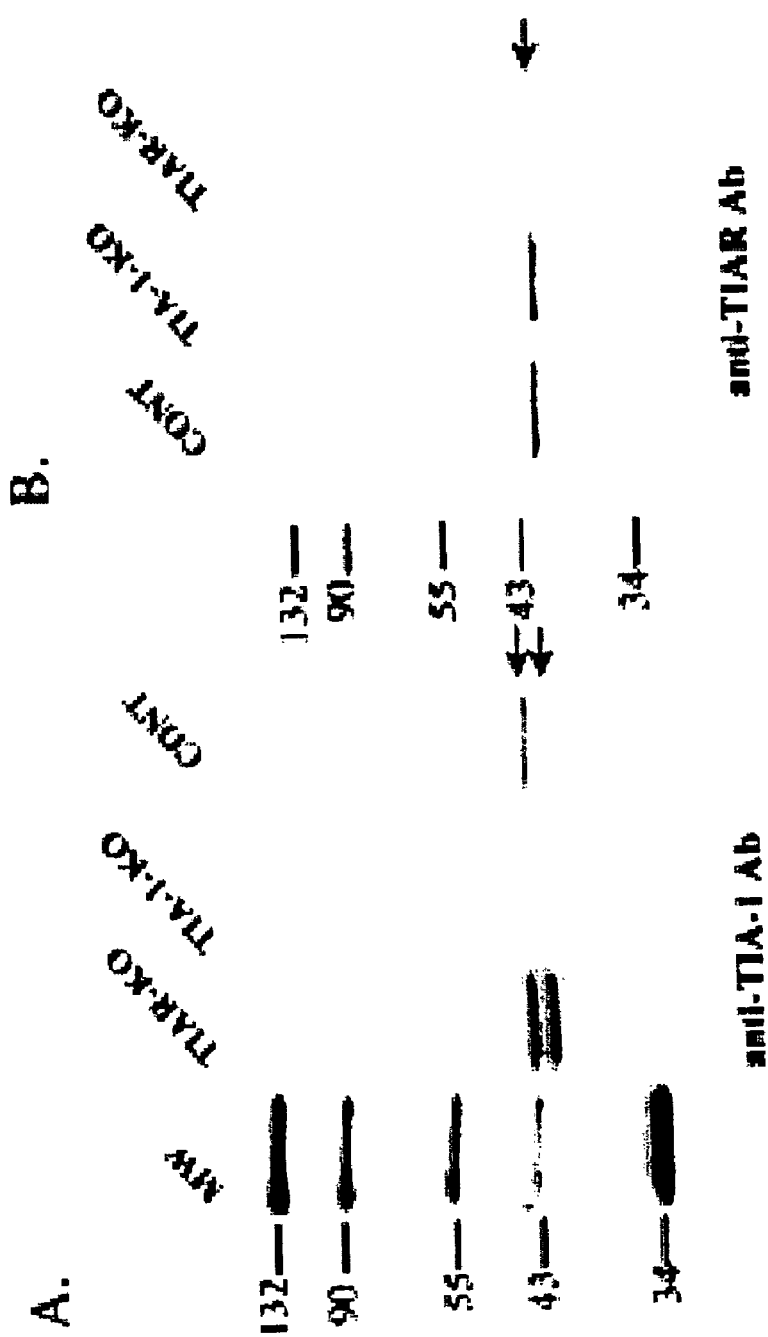
Figure 6C:
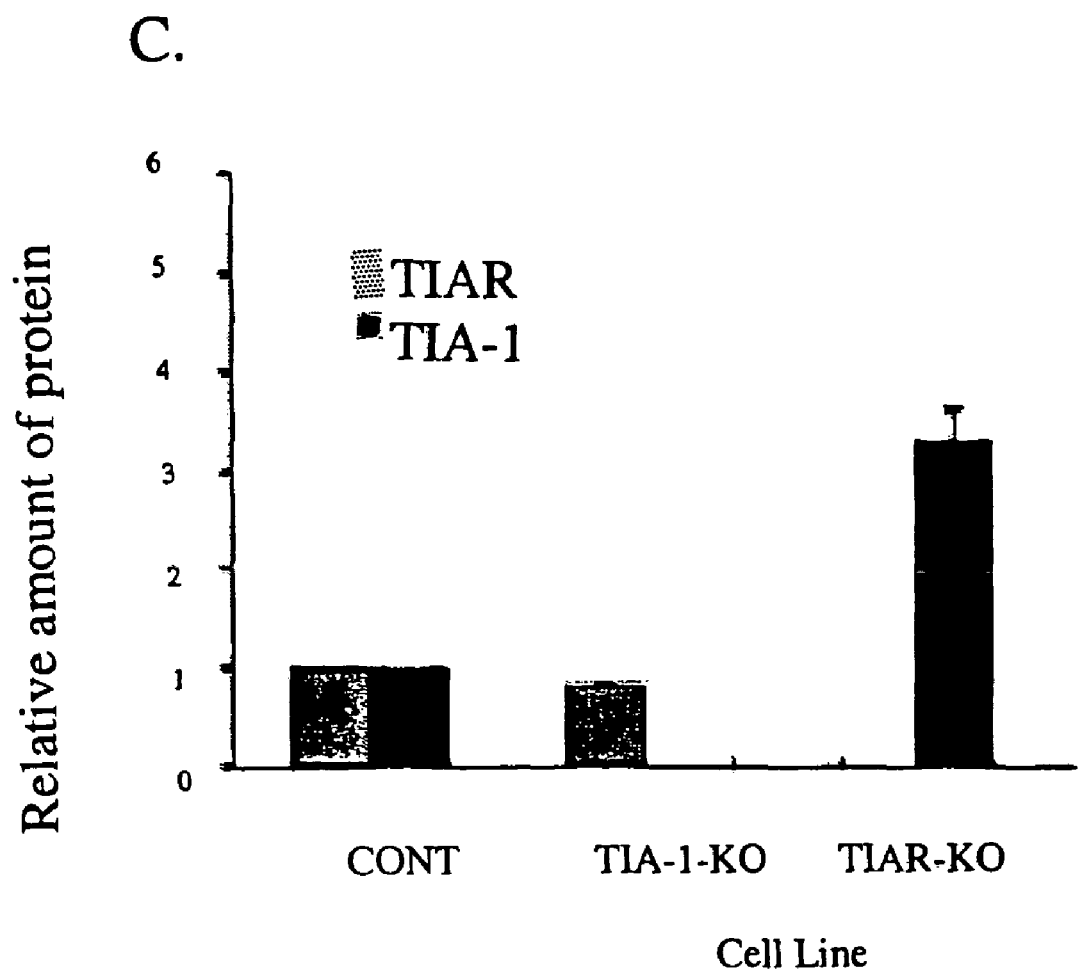
Figures 6D, 6E:
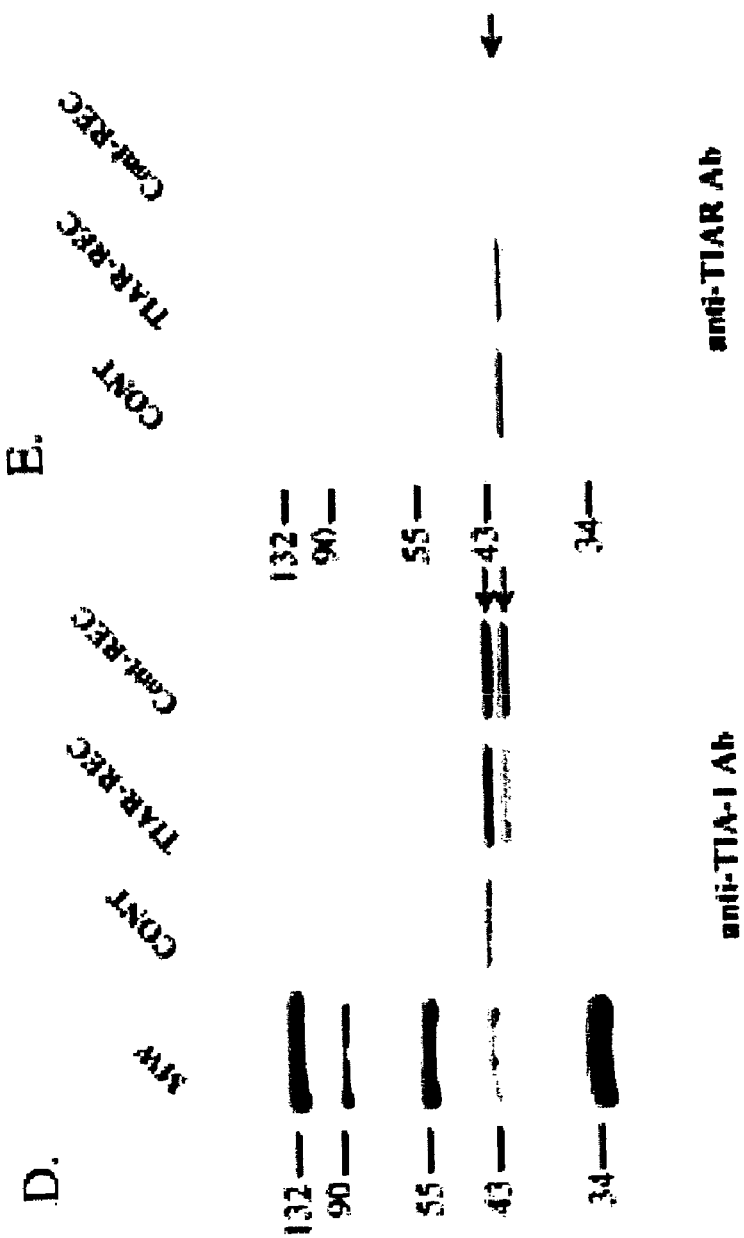
Figure 6F:
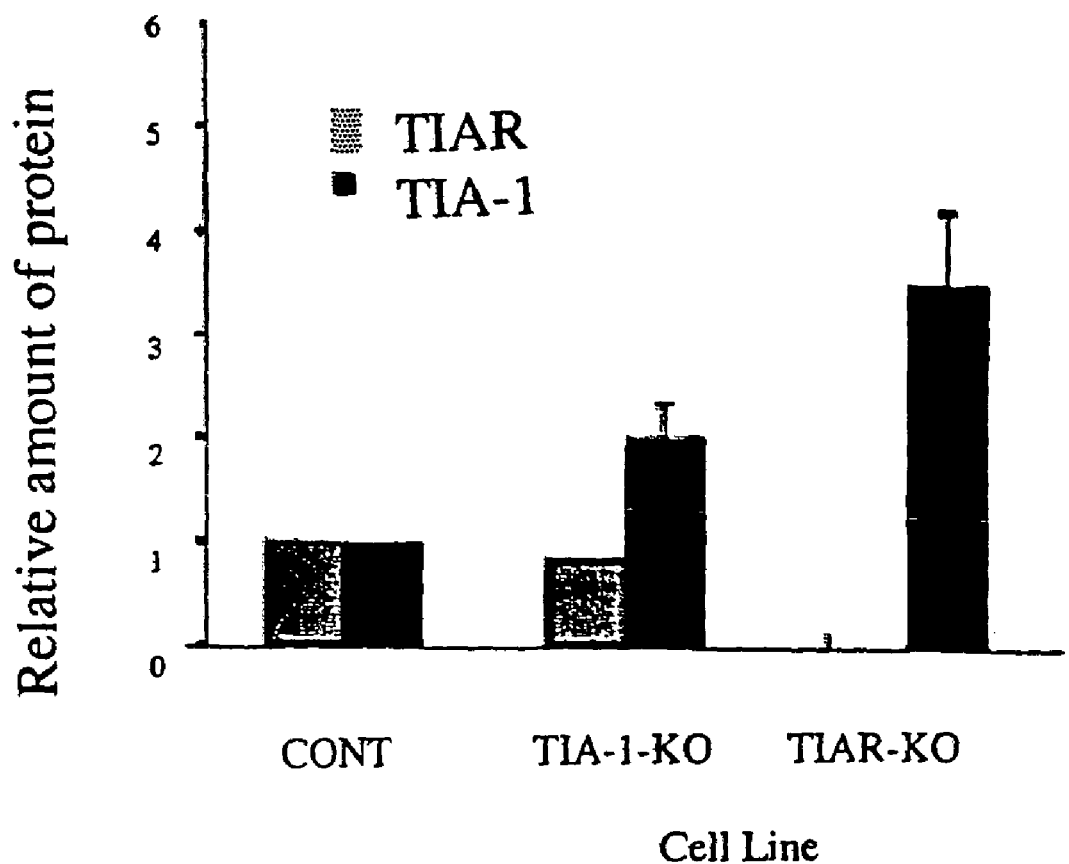

VSV (FIG. 5C) and Sindbis virus (FIG. 5D) grew to similar titers in TIAR-knockout and control cells, whereas in TIA-knockout cells, both of these viruses grew to significantly higher titers suggesting that the presence of TIA-1 had a negative effect on the growth of these viruses. HSV-1 also grew to significantly higher levels in TIA-1 knockout cells than in control cells (FIG. 6E). However, the growth of HSV-1 in TIAR-knockout cells was also more efficient than in control cells, but not as efficient as in TIA-knockout cells. The efficiency of growth of vaccinia virus (FIG. 5F) in all three types of cells was similar. Because the majority of the vaccinia progeny virus is cell associated, the extracellular virus titers detected were significantly lower than those for the other viruses. These results indicate that only the growth of WNV was less efficient in the TIAR-knockout cells.

Figure 5B:
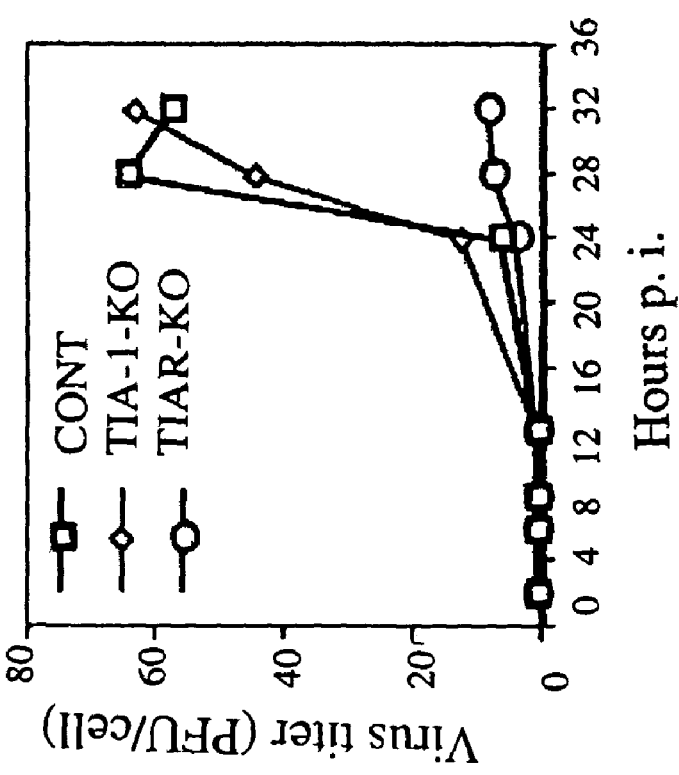
Figure 5C:
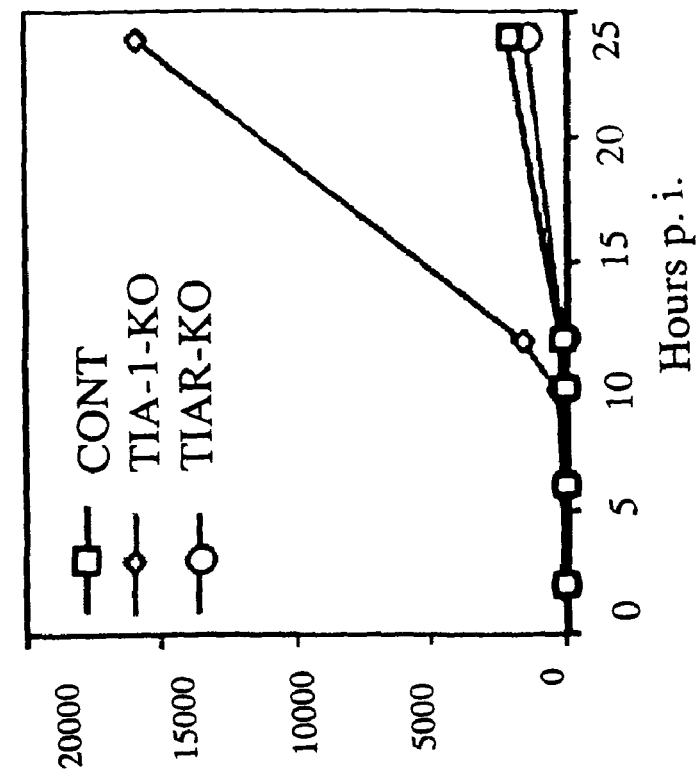
Figure 5D:
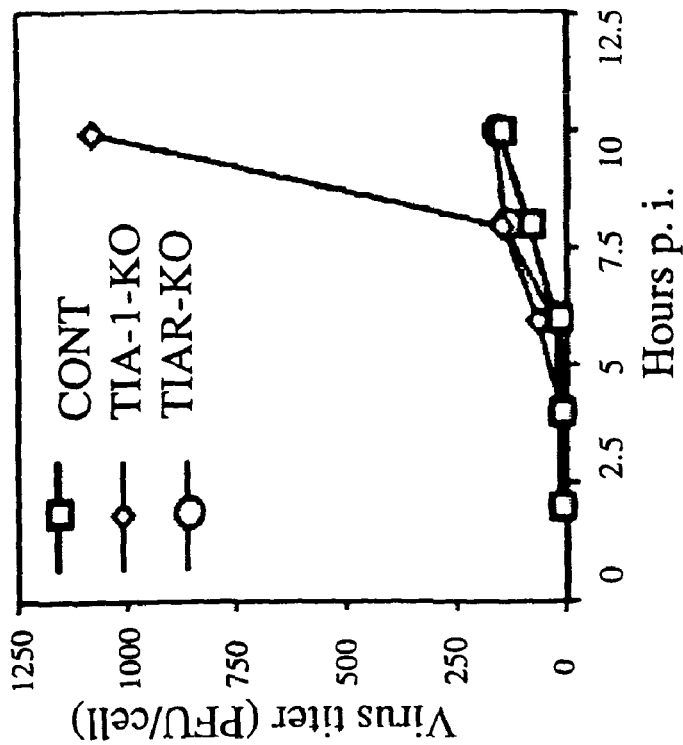
Figure 5E:
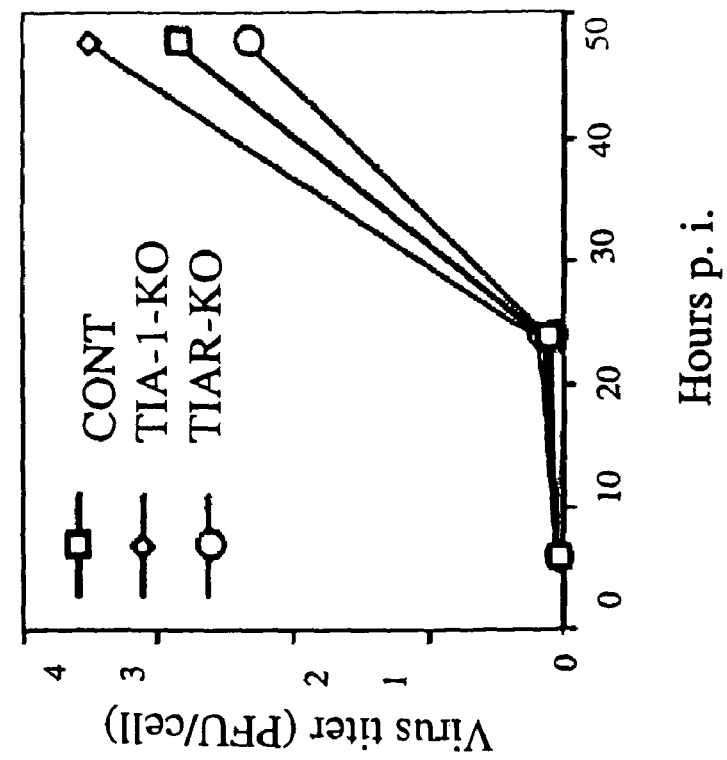
Figure 5F:
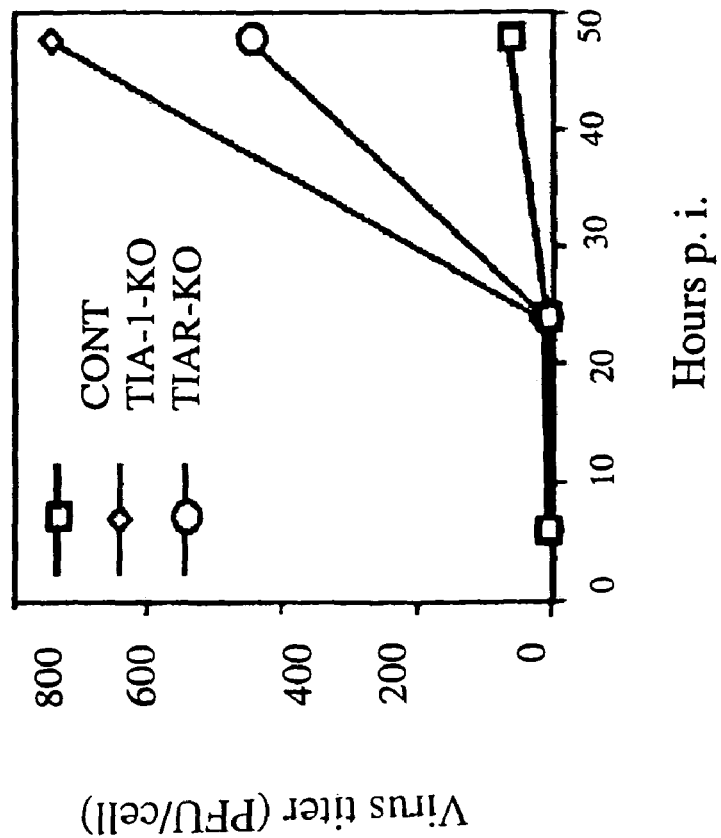

To further investigate the effect of TIAR on viral growth, the growth of WNV in a TIAR-reconstituted stable cell line, TIAR-REC, was tested. Another stable cell line, Cont-REC, which had been transfected with the same vector, but did not express TIAR at detectable levels (FIG. 6E), was used as a control for possible nonspecific effects of the vector. FIG. 5B shows representative WNV growth curves obtained with control, TIAR-REC and Cont-REC cells. Although the peak titer of WNV produced by TIAR-reconstituted cells was higher than that produced by Cont-REC cells, it was lower than that produced by control cells.

Example 8

Comparison of the Relative Amounts of TIAR and TIA-1 Proteins in the Various Cell Lines The relative amounts of TIAR and TIA-1 in cytoplasmic extracts from each of the cell lines were estimated by immunoblotting using protein-specific antibody. Previous studies showed that two isoforms generated by alternative splicing exist for both TIA-1 and TIAR (1). The two TIA-1 isoforms, 42 kDa TIA-1a and 40 kDa TIA-1b, differ from each other by an 11 amino acid deletion. These isoforms are usually found in cells in a 1:1 ratio. The two TIAR isoforms, 42 kDa TIARa and 40 kDa TIARb, differ from each other by a 17 amino acid deletion. Because TIARb is six times more abundant in cells than TIARa, it is the only isoform that is detected by Western blotting. Representative Western blots are shown (FIGS. 6A, B, D, and E). Twenty µg of total cell protein were run on each lane. The TIAR protein and two isoforms of the TIA-1 protein are indicated by arrows. Quantification of the relative amounts of protein in the various types of cells is shown in FIGS. 6C and F. The relative amount of each protein in the control cells was defined as 1. The relative amounts of the proteins in other cell lines were expressed as the ratio of the protein band intensity divided by the density of the band in control cells. The values shown are means of the values obtained from 3 to 5 separate experiments.

As expected, no TIA-1 protein was detected in cytoplasmic extracts from TIA-1-knockout cells (FIG. 6A) and no TIAR protein was detected in cytoplasmic extracts from TIAR-knockout cells (FIG. 6B). The level of the TIAR protein in cytoplasmic extracts from TIA-1 knockout cells ($a^{-/-}43$) was slightly decreased (FIG. 6B), but the amount of TIA-1 protein in the cytoplasm of TIAR-knockout cells was significantly increased (by 3.3 fold) as compared to the amounts of these proteins present in the control (W4) cells (FIGS. 6A and C). These data indicate that the level of TIA-1 is down-regulated by TIAR. No significant differences in the cytoplasmic levels of either protein were observed after WNV infection (at 5 or 8 hr p.i.) in the various cell lines tested (data not shown).

The amount of TIAR protein detected in the TIAR-REC cells was about 80% of that detected in control (W4) cells (FIGS. 6E and F), while no TIAR protein was detected in Cont-REC cells (FIG. 6E). The amount of TIA-1 protein in the TIAR-REC cells was 2 fold higher, while the amount of TIA-1 protein in Cont-REC cells was 3.5 fold higher, as compared to controlW4 cells (FIGS. 6D and F). These data indicate that the TIAR-REC cells had intermediate levels of the two proteins.

Example 9

Comparison of TIAR and TIA-1 cDNA Sequences from Cells Obtained from Flavivirus Resistant and Susceptible Mice A single, dominant gene, Flv, that maps to chromosome 5 confers a flavivirus resistance phenotype in mice. Data from previous studies showed that resistant mice as well as cells obtained from a number of different tissues of resistant mice produced significantly lower titers of flaviviruses than did congenic susceptible mice or cells and that genomic RNA levels, but not minus strand viral RNA levels, were lower in resistant cells (7; Li and Brinton, unpublished data). Since both TIAR and TIA-1 bind to the WNV 3'(−)SL RNA and this SL is located at the site of initiation of genomic RNA synthesis, it was of interest to determine whether the sequences of TIAR and TIA-1 cDNAs differed in cells from resistant C3H/He and congenic susceptible C3H.RV mice. Cell RNA was extracted from resistant and susceptible embryo fibroblasts with TRIZOL-LS (Life/Gibco) according to the manufacturer's instructions. Using primers designed from mouse (strain 129 SVJ) TIA-1 and TIAR cDNA sequences previously reported by Beck et al. (1996), cDNAs were amplified by RT-PCR from cell mRNA and TA cloned into pCR 2.1-TOPO (Invitrogen). At least three cDNA clones for each isoform were sequenced. The sequences obtained for the two TIAR isoform cDNAs and for the two TIA-1 isoform cDNAs from resistant C3H.RV were identical to those of the comparable isoforms obtained from susceptible C3H/HE cells. These sequences were also identical to the previously reported sequences for these proteins from 129SVJ mice (Accession numbers: U55861 and U55862) by Beck et al. (1). Also, as assessed by Western blotting, the expression levels of the TIAR and TIA-1 proteins in resistant cells and susceptible cells were similar. These data indicate that neither TIAR nor TIA-1 is the product of the Flv gene.

All references and patents cited herein are hereby incorporated in their entireties.

References

1. Beck, A. R., Q. G. Medley, S. O'Brien, P. Anderson, and M. Streuli 1996. Structure, tissue distribution and genomic organization of the murine RRM-type RNA binding proteins TIA-1 and TIAR Nucleic Acids Res. 24:3829-35.

2. Beck, A. R., I. J. Miller, P. Anderson, and M. Streuli 1998. RNA-binding protein TIAR is essential for primordial germ cell development Proc Natl Acad Sci USA. 95:2331-6.

3. Blackwell, J. L., and M. A. Brinton 1995. BHK cell proteins that bind to the 3' stem-loop structure of the West Nile virus genome RNA J Virol. 69:5650-8.

4. Blyn, L. B., K. M. Swiderek, O. Richards, D. C. Stahl, B. L. Semler, and E. Ehrenfeld 1996. Poly(rC) binding protein 2 binds to stem-loop IV of the poliovirus RNA 5' noncoding region: identification by automated liquid chromatography-tandem mass spectrometry Proc Natl Acad Sci U S A. 93:11115-20.

5. Blyn, L. B., J. S. Towner, B. L. Semler, and E. Ehrenfeld 1997. Requirement of poly(rC) binding protein 2 for translation of poliovirus RNA J Virol. 71:6243-6.

6. Brand, S., and H. M. Bourbon 1993. The developmentally-regulated *Drosophila* gene rox8 encodes an RRM-type RNA binding protein structurally related to human TIA-1-type nucleolysins Nucleic Acids Res. 21:3699-704.

7. Brinton, M. A. 1997. Host susceptibility to viral disease, p. 303-328. In N. N. e. al (ed.), Viral Pathogenesis. Lippincott-Raven Publishers, Philadelphia.

8. Brinton, M. A., and J. H. Dispoto 1988. Sequence and secondary structure analysis of the 5'-terminal region of flavivirus genome RNA Virology. 162:290-9.

9. Brinton, M. A., A. V. Fernandez, and J. H. Dispoto 1986. The 3'-nucleotides of flavivirus genomic RNA form a conserved secondary structure Virology. 153:113-21.

10. Burke, D. S., and T. P. Monath 2001. Flaviviruses, p. 1043-1125. In D. M. Knipe, and P. M. Howley (eds), Fields Virology. Lippencott Williams and Wilkins, Philadelphia.

11. Davanloo, P., A. H. Rosenberg, J. J. Dunn, and F. W. Studier 1984. Cloning and expression of the gene for bacteriophage T7 RNA polymerase Proc Natl Acad Sci U S A. 81:2035-9.

12. Davis, M. T., and T. D. Lee 1998. Rapid protein identification using a microscale electrospray LC/MS system on an ion trap mass spectrometer J Am Soc Mass Spectrom. 9:194-201.

13. Davis, M. T., and T. D. Lee 1997. Variable flow liquid chromatography-tandem mass spectrometry and the comprehensive analysis of complex protein digest mixtures J Am Soc Mass Spectrom. 8:1059-1069.

14. Del Gatto-Konczak, F., C. F. Bourgeois, C. Le Guiner, L. Kister, M. C. Gesnel, J. Stevenin, and R. Breathnach 2000. The RNA-binding protein TIA-1 is a novel mammalian splicing regulator acting through intron sequences adjacent to a 5' splice site Mol Cell Biol. 20:6287-99.

15. Dember, L. M., N. D. Kim, K. Q. Liu, and P. Anderson 1996. Individual RNA recognition motifs of TIA-1 and TIAR have different RNA binding specificities J Biol Chem. 271:2783-8.

16. Forch, P., and J. Valcarcel 2001. Molecular mechanisms of gene expression regulation by the apoptosis-promoting protein TIA-1 Apoptosis. 6:463-8.

17. Fukui, Y., S. Yumura, and T. K. Yumura 1987. Agar-overlay immunofluorescence: high-resolution studies of cytoskeletal components and their changes during chemotaxis Methods Cell Biol. 28:347-56.

18. Gueydan, C., L. Droogmans, P. Chalon, G. Huez, D. Caput, and V. Kruys 1999. Identification of TIAR as a protein binding to the translational regulatory AU-rich element of tumor necrosis factor alpha mRNA J Biol Chem. 274:2322-6.

19. Jessen, T. H., C. Oubridge, C. H. Teo, C. Pritchard, and K. Nagai 1991. Identification of molecular contacts between the U1 A small nuclear ribonucleoprotein and U1 RNA Embo J. 10:3447-56.

20. Kawakami, A., Q. Tian, X. Duan, M. Streuli, S. F. Schlossman, and P. Anderson 1992. Identification and functional characterization of a TIA-1-related nucleolysin Proc Natl Acad Sci USA. 89:8681-5.

21. Kedersha, N., S. Chen, N. Gilks, W. Li, I. J. Miller, J. Stahl, and P. Anderson 2002. Evidence That Ternary Complex (eIF2-GTP-tRNA(i)(Met))-Deficient Preinitiation Complexes Are Core Constituents of Mammalian Stress Granules Mol Biol Cell. 13:195-21.

22. Kedersha, N. L., M. Gupta, W. Li, I. Miller, and P. Anderson 1999. RNA-binding proteins TIA-1 and TIAR link the phosphorylation of eIF-2 alpha to the assembly of mammalian stress granules J Cell Biol. 147:1431-42.

23. Kim, Y. J., and B. S. Baker 1993. Isolation of RRM-type RNA-binding protein genes and the analysis of their relatedness by using a numerical approach Mol Cell Biol. 13:174-83.

24. Lanciotti, R. S., J. T. Roehrig, V. Deubel, J. Smith, M. Parker, K. Steele, B. Crise, K. E. Volpe, M. B. Crabtree, J. H. Scherret, R. A. Hall, J. S. MacKenzie, C. B. Cropp, B. Panigrahy, E. Ostlund, B. Schmitt, M. Malkinson, C. Banet, J. Weissman, N. Komar, H. M. Savage, W. Stone, T. McNamara, and D. J. Gubler 1999. Origin of the West Nile virus responsible for an outbreak of encephalitis in the northeastern United States Science. 286:2333-7.

25. Le Guiner, C., F. Lejeune, D. Galiana, L. Kister, R. Breathnach, J. Stevenin, and F. Del Gatto-Konczak 2001. TIA-1 and TIAR Activate Splicing of Alternative Exons with Weak 5' Splice Sites followed by a U-rich Stretch on Their Own Pre-mRNAs J Biol Chem. 276:40638-46.

26. Lewis, T., C. Gueydan, G. Huez, J. J. Toulme, and V. Kruys 1998. Mapping of a minimal AU-rich sequence required for lipopolysaccharide-induced binding of a 55-kDa protein on tumor necrosis factor-alpha mRNA J Biol Chem. 273:13781-6.

27. Lindenbach, B. D., and C. M. Rice 2001. Flaviviridae: The viruses and their replication, p. 991-1041. In D. M. Knipe, and P. M. Howley (eds), Fields Virology. Lippencott Williams and Wilkins, Philadelphia.

28. Lu, C. D., J. E. Houghton, and A. T. Abdelal 1992. Characterization of the arginine repressor from *Salmonella typhimurium* and its interactions with the carAB operator J Mol Biol. 225:11-24.

29. Mackenzie, J. M., M. K. Jones, and E. G. Westaway 1999. Markers for trans-Golgi membranes and the intermediate compartment localize to induced membranes with distinct replication functions in flavivirus-infected cells J Virol. 73:9555-67.

30. Mackenzie, J. M., A. A. Khromykh, M. K. Jones, and E. G. Westaway 1998. Subcellular localization and some biochemical properties of the flavivirus Kunjin nonstructural proteins NS2A and NS4A Virology. 245:203-15.

31. Men, R., M. Bray, D. Clark, R. M. Chanock, and C. J. Lai 1996. Dengue type 4 virus mutants containing deletions in the 3' noncoding region of the RNA genome: analysis of growth restriction in cell culture and altered viremia pattern and immunogenicity in rhesus monkeys J Virol. 70:3930-7.

32. Parquet, M. C., A. Kumatori, F. Hasebe, K. Morita, and A. Igarashi 2001. West Nile virus-induced bax-dependent apoptosis FEBS Lett. 500:17-24.

33. Piecyk, M., S. Wax, A. R. Beck, N. Kedersha, M. Gupta, B. Maritim, S. Chen, C. Gueydan, V. Kruys, M. Streuli, and P. Anderson 2000. TIA-1 is a translational silencer that selectively regulates the expression of TNF-alpha Embo J. 19:4154-63.

34. Rice, C. M. 1996. Fields Virology, 3 rd Edition ed. ed. Lippincott-Raven Publishers, Philadelphia.

35. Sambrook, J., E. F. Fritsch, and T. Maniatis 1989. Molecular cloning: a laboratory manual., 2 nd ed. ed. Cold Spring Harbor Laboratory Press, Cold Spring Harbor, N.Y.

36. Shi, P. Y., M. A. Brinton, J. M. Veal, Y. Y. Zhong, and W. D. Wilson 1996. Evidence for the existence of a pseudoknot structure at the 3' terminus of the flavivirus genomic RNA Biochemistry. 35:4222-30.

37. Shi, P. Y., W. Li, and M. A. Brinton 1996. Cell proteins bind specifically to West Nile virus minus-strand 3' stem-loop RNA J Virol. 70:6278-87.

38. Swiderek, K. M., M. T. Davis, and T. D. Lee 1998. The identification of peptide modifications derived from gel-separated proteins using electrospray triple quadrupole and ion trap analyses Electrophoresis. 19:989-97.

39. Taupin, J. L., Q. Tian, N. Kedersha, M. Robertson, and P. Anderson 1995. The RNA-binding protein TIAR is translocated from the nucleus to the cytoplasm during Fas-mediated apoptotic cell death Proc Natl Acad Sci U S A. 92:1629-33.

40. Tian, Q., M. Streuli, H. Saito, S. F. Schlossman, and P. Anderson 1991. A polyadenylate binding protein localized to the granules of cytolytic lymphocytes induces DNA fragmentation in target cells Cell. 67:629-39.

41. Tian, Q., J. Taupin, S. Elledge, M. Robertson, and P. Anderson 1995. Fas-activated serine/threonine kinase (FAST) phosphorylates TIA-1 during Fas-mediated apoptosis J Exp Med. 182:865-74.

42. Vaheri, A., W. D. Sedwick, S. A. Plotkin, and R. Maes 1965. Cytopathic effect of rubella virus in RHK21 cells and growth to high titers in suspension culture Virology. 27:239-41.

43. Weeks, K. M., and D. M. Crothers 1992. RNA binding assays for Tat-derived peptides: implications for specificity Biochemistry. 31:10281-7.

44. Wilson, R., R. Ainscough, K. Anderson, C. Baynes, M. Berks, J. Bonfield, J. Burton, M. Connell, T. Copsey, J. Cooper, and et al. 1994. 2.2Mb of contiguous nucleotide sequence from chromosome III of *C. elegans* [see comments] Nature. 368:32-8.

45. Zeng, L., B. Falgout, and L. Markoff 1998. Identification of specific nucleotide sequences within the conserved 3'-SL in the dengue type 2 virus genome required for replication J Virol. 72:7510-22.

46. Blackwell, J. B. and Brinton, M. A. 1997. Translation elongation factor-1α interacts with the 3' stem-loop of West Nile virus genome RNA. J. Virol. 71: 6433-44.

47. Brinton, M. A., Fernandez, A. V. and Dispoto, J. H. 1986. The 3'-nucleotides of flavivirus genomic RNA form a conserved secondary structure. Virology 153:113-21.

What is claimed is:

1. A method of inhibiting replication of a West Nile Virus in a cell, the method comprising:
   infecting the cell with the West Nile Virus;
   providing to the cell an effective amount of a nucleic acid construct consisting of the 75 3' terminal nucleotides of the negative strand nucleic acid of a West Nile Virus, the 3' terminal nucleotides comprising a stem loop structure with a first single-stranded loop and a second-single stranded loop, the first-single stranded loop comprising a nucleotide sequence of UAAU and the second-single stranded loop comprising a nucleotide sequence of UUAAU, wherein the first single-stranded loop and the second-single stranded loop are capable of associating with at least one host-cell protein, wherein the at least one host-cell protein is T-cell intracellular antigen-related (TIAR) protein or T-cell intracellular antigen-1 (TIA-1) protein; and wherein the nucleic acid construct inhibits replication of the West Nile Virus in the infected cell by inhibiting or interfering with the binding between the at least one host-cell protein in the cell and a negative strand RNA of the infecting West Nile Virus.

2. The method of inhibiting replication of the West Nile Virus of claim 1, wherein the infecting the cell with the West Nile Virus occurs before the providing to the cell an effective amount of the nucleic acid construct comprising the 3' stem loop structure of the negative strand nucleic acid of West Nile Virus.

3. The method of inhibiting replication of the West Nile Virus of claim 1, wherein the infecting the cell with the West Nile Virus occurs after the providing to the cell an effective amount of the nucleic acid construct comprising the 3' stem loop structure of the negative strand nucleic acid of the West Nile Virus.

4. An assay for determining compositions that inhibit West Nile Virus replication in the cytoplasm of cells, the assay comprising,
   a) adding a test composition to the cells, wherein the cells are infected with the West Nile Virus,
   b) comparing the change in the West Nile Virus replication of the cells of a) to replication in control cells infected with the West Nile Virus in the absence of the test composition and determining whether the test composition of a) inhibits the replication of the West Nile Virus;
   c) comparing the change in the West Nile Virus replication of the cells of a) to replication in knockout cells infected with the West Nile Virus; wherein the knockout cells have a deletion or a disruption of at least one gene encoding at least one protein, and wherein the at least one protein is TIAR or TIA-1, wherein if the replication is inhibited in the presence of the test composition compared to the absence of the test composition, the test composition comprises a composition that inhibits West Nile Virus replication, and wherein if the replication is inhibited by the test composition to levels of replication by the knock-out cells then the test composition may function by inhibiting binding of the TIA protein or the TIAR protein to a 3' stem loop structure of a negative strand nucleic acid of the West Nile Virus.

5. The assay of claim 4, wherein the change in viral replication is a change in the rate of replication of the virus or a change in the amount of viral components synthesized.

6. The assay for determining compositions that inhibit the West Nile Virus replication in the cytoplasm of the cells of claim 4, wherein the composition is a nucleic acid construct.

7. The assay for determining compositions that inhibit the West Nile Virus replication in the cytoplasm of the cells of claim 6, wherein the nucleic acid construct is a nucleic acid construct comprising a 3' stem loop structure of a negative strand nucleic acid of West Nile Virus comprising the 75 3' terminal nucleotides of the negative strand nucleic acid of West Nile Virus.

8. A method of treating a West Nile Virus infection, the method comprising:
   providing to a human cell or an animal cell having the West Nile Virus infection, a nucleic acid construct, the nucleic acid construct consisting of the 75 3' terminal nucleotides of the negative strand nucleic acid of a West Nile Virus, the 3' terminal nucleotides comprising a stem loop structure with a first single-stranded loop and a second-single stranded loop, the first single-stranded loop comprising a nucleotide sequence of UAAU and the second-single stranded loop comprising a nucleotide sequence of UUAAU,
   wherein the first-single-stranded loop and the second single-stranded loop are capable of associating with at least one host-cell protein, wherein the at least one host-cell protein is TIAR or TIA 1, and wherein the nucleic acid construct inhibits replication of the West Nile Virus in the infected cell by inhibiting or interfering with the binding between the at least one host-cell protein in the cell and a negative strand RNA of the infecting West Nile Virus.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Inovirus C2

<400> SEQUENCE: 1
caggaaacag ctatgaccat g                                        21

<210> SEQ ID NO 2
<211> LENGTH: 20
<212> TYPE: DNA
<213> ORGANISM: Inovirus C2

<400> SEQUENCE: 2
agtagttcgc ctgtgtgagc                                          20

<210> SEQ ID NO 3
<211> LENGTH: 75
<212> TYPE: RNA
<213> ORGANISM: West Nile virus

<400> SEQUENCE: 3
```

-continued

```
cagcucgcac gguguuaauu guuguuaauc cucacaaaca cuacuaaguu ugucagcuca    60
cacaggcgaa cuacu                                                    75
```